(12) United States Patent
Loskutoff et al.

(10) Patent No.: US 7,405,036 B2
(45) Date of Patent: Jul. 29, 2008

(54) PROCESS FOR REDUCING PATHOGENS IN A BIOLOGICAL SAMPLE AND REMOVING A SAMPLE PELLET FROM A SAMPLE TUBE

(75) Inventors: Naida M. Loskutoff, Omaha, NE (US); Kari Morfeld, Burke, VA (US); James Dow, Edina, MN (US)

(73) Assignee: Safety Art, LLC, Omaha, NE (US)

( * ) Notice: Subject to any disclaimer, the term of this patent is extended or adjusted under 35 U.S.C. 154(b) by 409 days.

(21) Appl. No.: 10/900,061

(22) Filed: Jul. 26, 2004

(65) Prior Publication Data

US 2005/0064579 A1 Mar. 24, 2005

Related U.S. Application Data

(63) Continuation-in-part of application No. PCT/US02/16082, filed on May 21, 2002.

(60) Provisional application No. 60/489,819, filed on Jul. 24, 2003, provisional application No. 60/489,832, filed on Jul. 24, 2003, provisional application No. 60/292,723, filed on May 21, 2001, provisional application No. 60/293,249, filed on May 24, 2001, provisional application No. 60/293,713, filed on May 25, 2001, provisional application No. 60/294,196, filed on May 29, 2001, provisional application No. 60/295,255, filed on Jun. 1, 2001.

(51) Int. Cl.
*A01N 1/02* (2006.01)
*C12N 5/00* (2006.01)
*C07G 15/00* (2006.01)

(52) U.S. Cl. .................. 435/2; 435/268; 435/308.1; 436/175; 436/177

(58) Field of Classification Search ............. 435/2, 435/308.1; 422/72, 101; 436/175, 177
See application file for complete search history.

(56) References Cited

U.S. PATENT DOCUMENTS 4,435,293 A * 3/1984 Graham et al. ............... 210/772

(Continued)

FOREIGN PATENT DOCUMENTS

WO WO 02094739 A2 * 11/2002

*Primary Examiner*—William H Beisner
(74) *Attorney, Agent, or Firm*—Suiter Swantz pc llo

(57) ABSTRACT

The present invention is directed towards an apparatus and method for disinfecting biological samples, including semen and the like, and for removing a biological sample pellet from surrounding media while reducing the risk of recontamination of the pellet with said media. An insert receptacle includes a receiving cylinder having a drain in a floor which allows the fluids to decant slowly down the side of a tube. The insert receptacle further includes an aspiration channel which allows an aspiration device, such as a modified micro-pipette, to be utilized for extracting a sample pellet from the bottom of the tube. Utilizing the novel apparatus, a method for reducing pathogens in a biological sample includes decanting the biological sample through the receiving cylinder and into a tube where it passes through a multi-layer gradient including an enzyme suitable for removal of at least one pathogen from the biological sample. Centrifuging of the insert receptacle, tube, and sample, isolates a sample pellet of the biological sample from the surrounding at least one pathogen. After the sample pellet is isolated it is aspirated via the aspiration device without re-contaminating the sample pellet through contact with the surrounding at least one pathogen.

2 Claims, 21 Drawing Sheets

U.S. PATENT DOCUMENTS 5,681,709 A * 10/1997 Mochnal et al. ............ 435/7.25
2002/0185457 A1 * 12/2002 Smith et al. ................ 210/787
2005/0079480 A1 * 4/2005 Loskutoff ..................... 435/2

* cited by examiner

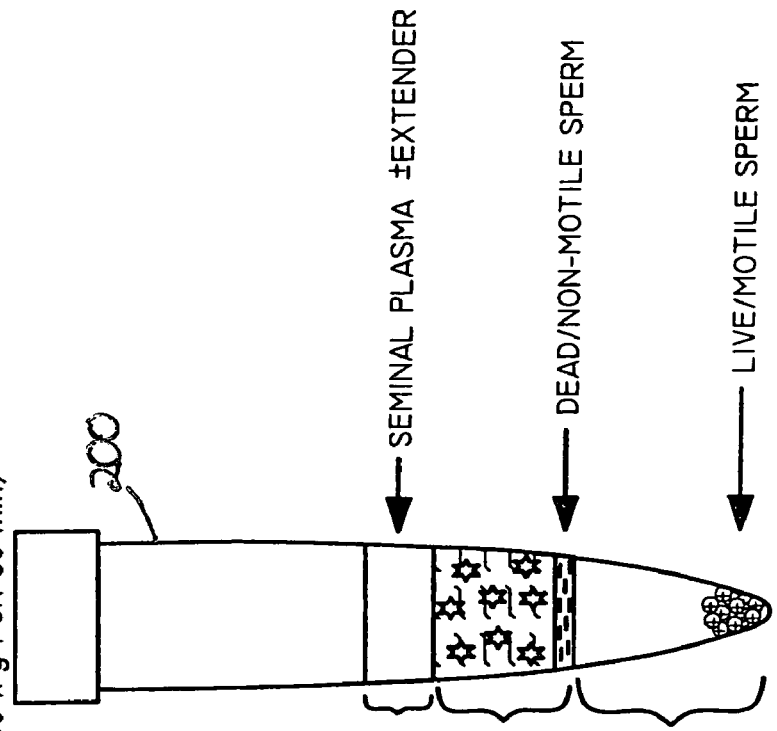
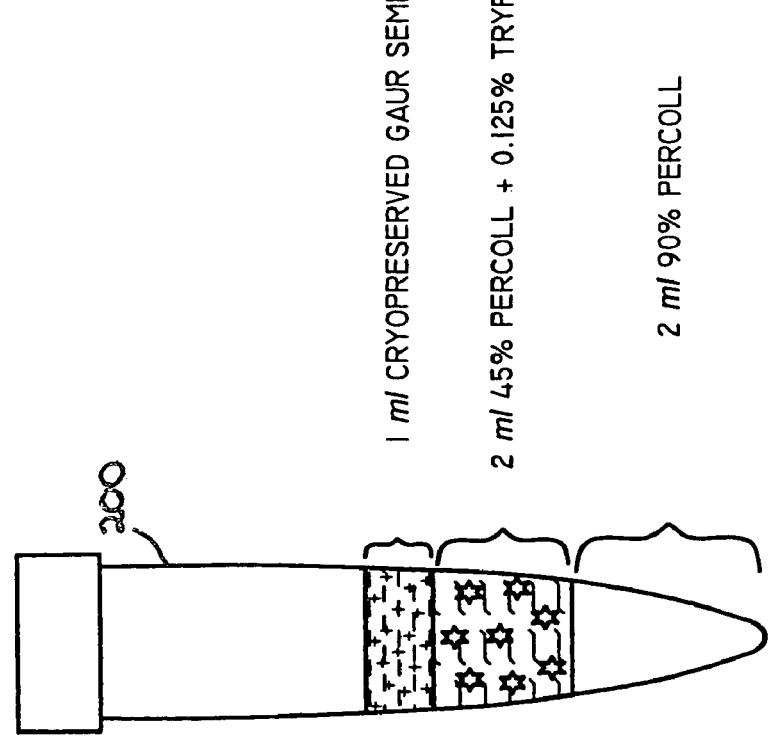
FIG. 6A

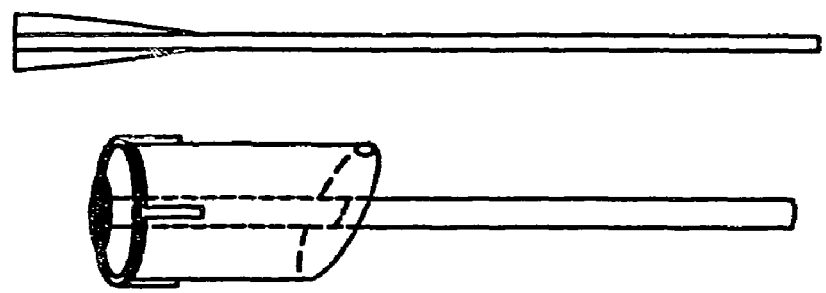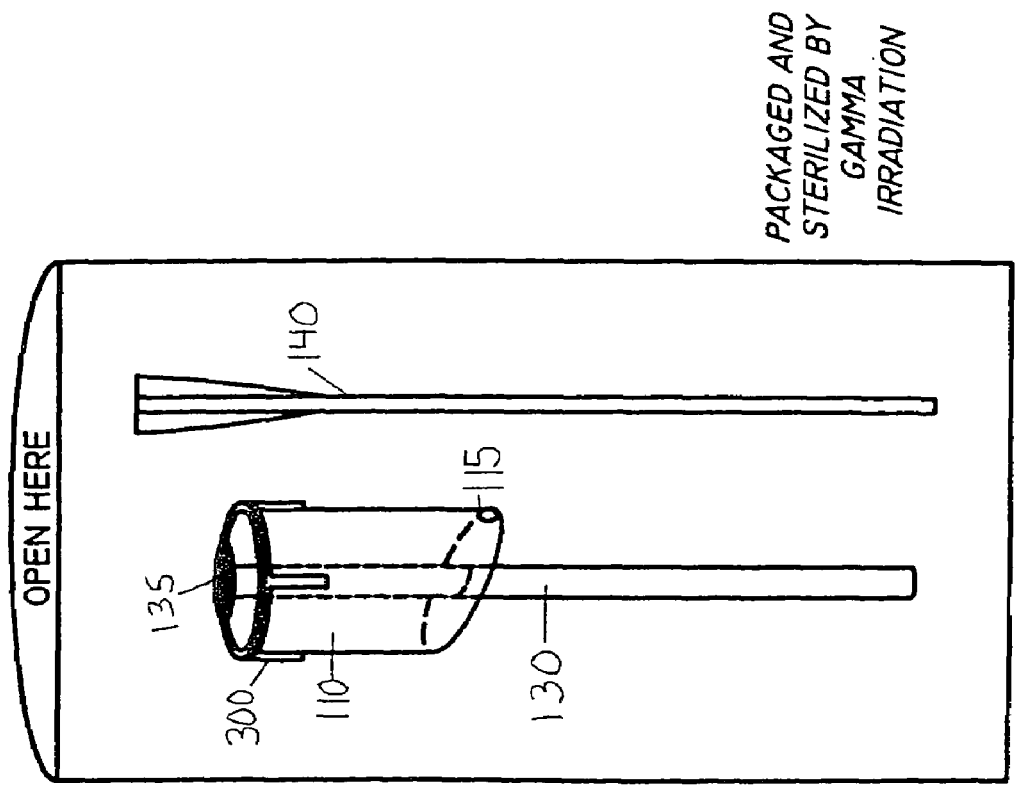
FIG. 11A

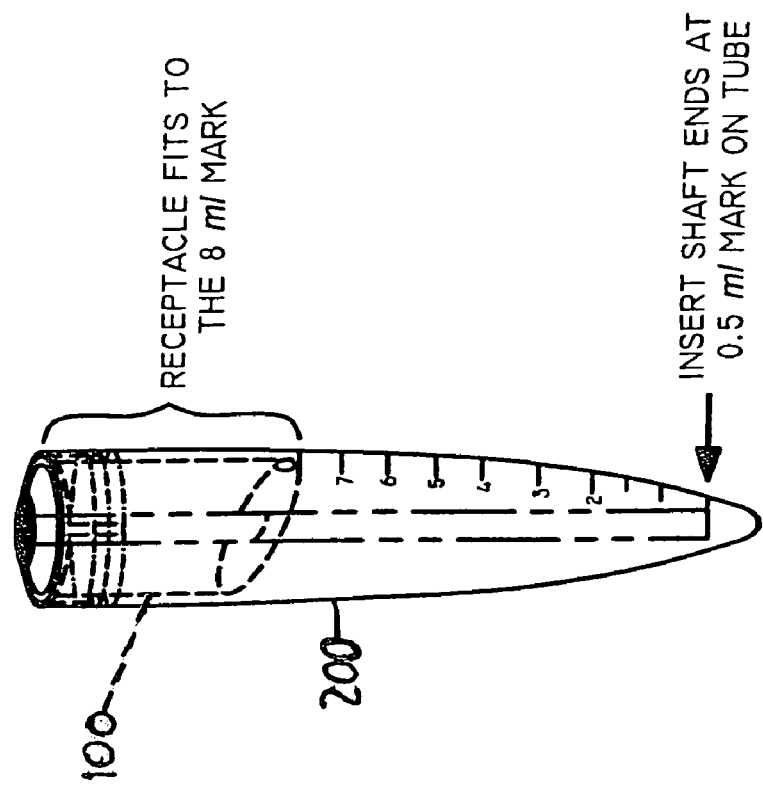
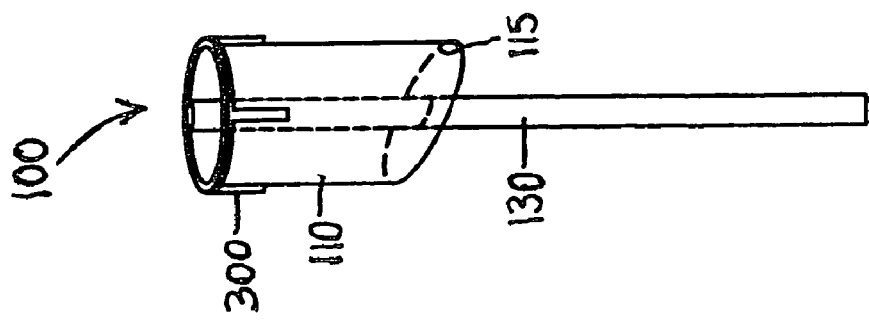
FIG. 11B

DOSE-RESPONSE OF DECREASING CONCENTRATIONS OF
SOY-BASED TRYPSIN INACTIVATOR IN 90% ISOLATE ON ITS
ABILITY TO DETACH CONFLUENT BRL MONOLAYERS

− = NO DETACHMENT NOTED (TRYPSIN INACTIVE);
+ = CELLS DETACHING (TRYPSIN ACTIVE)

LOWEST EFFECTIVE DOSE: 10 μg/ml

| SOY TRYPSIN INACTIVATOR mg/mL: | 1.4 (n=1) | 0.35 (n=1) | 0.15 (n=1) | 0.08 (n=1) | 0.02 (n=1) | 0.01 (n=3) | 0.005 (n=3) | 0.0025 (n=1) | 0.0006 (n=1) |
|---|---|---|---|---|---|---|---|---|---|
| 0.25% TRYPSIN | − | − | − | − | − | 1. −<br>2. −<br>3. − | 1. −<br>2. −<br>3. ROUNDED AT 5 MIN;<br>>90% DETACHED AT 10 MIN | +<br>ROUNDED AT 3 MIN | +<br>ROUNDED AT 3 MIN; >90% DETACHED AT 10 MIN |
| 0.125% TRYPSIN | − | − | − | − | − | 1. −<br>2. −<br>3. − | 1. −<br>2. −<br>3. ROUNDED AT 5 MIN;<br>>90% DETACHED AT 10 MIN | | +<br>ROUNDED AT 3 MIN; >90% DETACHED AT 10 MIN |

FIG. 15

PROCESS FOR REDUCING PATHOGENS IN A BIOLOGICAL SAMPLE AND REMOVING A SAMPLE PELLET FROM A SAMPLE TUBE

CROSS REFERENCE TO RELATED APPLICATIONS

The present application claims priority under 35 U.S.C. §119(e) to the U.S. Provisional Application Ser. No. 60/489,819, filed on Jul. 24, 2003, and the U.S. Provisional Application Ser. No. 60/489,832, filed on Jul. 24, 2003. The present application is also a continuation-in-part of PCT Patent Application PCT/US02/16082, filed May 21, 2002, which in-turn, claims priority under 35 U.S.C. §119(e) to the following United States Provisional Patent Applications: U.S. Patent Application 60/292,723, filed May 21, 2001; U.S. Patent Application 60/293,249, filed May 24, 2001; U.S. Patent Application 60/293,713, filed May 25, 2001; U.S. Patent Application 60/294,196, filed May 29, 2001; and U.S. Patent Application 60/295,255, filed Jun. 1, 2001. All of the aforementioned applications are incorporated herein by reference in their entireties.

FIELD OF THE INVENTION

The present invention generally relates to the field of contaminate reduction in sample pellets (i.e., biological and non-biological), and particularly to an apparatus and method for decontamination and removal of a sample pellet from a sample tube.

BACKGROUND OF THE INVENTION

Effective processes to remove surrounding media from sample pellets (i.e., biological and non-biological) generally involve aspiration of the surrounding media and then, resuspension of the sample pellet while in the same tube with desired solution. Although such processes are effective at removing the majority of surrounding media, residual media remains on the sides of the tube and directly above the pellet surface resulting in the risk of contamination of the pellet with surrounding media upon pellet removal or pellet resuspension.

In addition, direct sample pellet extraction in the presence of the surrounding media requires the pellet to pass through the surrounding media, again, increasing the risk of pellet contamination. For example, a great risk exists concerning transmission of pathogenic agents in biological samples, such as seminal fluid. Semen samples obtained from men infected with pathogens such as HIV and Hepatitis B and C if not decontaminated prior to being used in artificial insemination, in vitro fertilization, or other assisted reproductive technology, may result in the infectious agents being transmitted to the mother, unborn child or health care workers handling the contaminated semen samples. Further, similar risks exist in animal or livestock industries which are utilizing assisted reproductive technology. In livestock, for example, the foot-and-mouth disease virus and porcine reproductive and respiratory syndrome (PRRS) virus have been shown to have devastating consequences to the national and international agricultural economies. As a result of such disease outbreaks, stricter regulations and sometimes bans on importation of animals or semen have been enacted which, in turn, affect animal and livestock industries by cutting off supplies and sources of new genetic materials.

There are currently no methods or apparatus for performance of these methods available that allow direct removal of a biological or non-biological sample pellet without first removing the surrounding media by aspiration or re-exposing the sample pellet to said media. As stated previously, such techniques are inherently flawed because of the likelihood of transferring contaminating agents in the surrounding media back to the sample pellets (e.g., directly from the pipette or indirectly from contaminated materials running down the side of the tube during aspiration).

It became known that such a process and apparatus would be desirable on September 24, 1999 at the Wild Cattle and Buffalo Taxon Advisory Group (TAG) meeting that was held at the annual conference of the American Zoo and Aquarium Association (AZA) in Minneapolis, Minn. At that meeting, a call was made for the formation of a task force by reproductive biologists collaborating or working directly with zoos to increase the research and development of assisted reproductive techniques (e.g., artificial insemination and embryo transfer) for non-domestic animals.

The reason for the alarm was due to the news of the possible closure of the last quarantine station available to animals which are to be exported from Africa and Asia after serving the USDA-mandated quarantine period (60 days outside the United States followed by 30 days within the United States). The station is in Poland and news that this country was going to join the European Union meant that they would be required to follow German guidelines which, consequently, would prohibit the entry of these animals to the quarantine station. Thus, it was hypothesized that assisted reproductive technology would become the only method by which the USDA Animal and Plant Health Inspection Service (APHIS) would allow importation of new genetic lines for captive ungulates (hoofed species such as antelope, deer, buffalo, and the like) and suids (exotic pig species) into American zoos.

At the meeting it was recognized that effective processes and apparatus to perform such processes to reduce or eliminate contamination in sperm samples which do not result in damage to the sperm are not currently available. As a result, the decision was made to focus more research on pathogen (e.g., microorganisms and viruses that create disease) interactions with the spermatozoa and embryos of wildlife species.

It was realized that there had been significant progress on developing methods for "disinfecting" embryos of specific pathogens. Such studies had a direct effect on the OIE and, as a consequence, the USDA APHIS, in lowering restrictions for the international movement of embryos, so long as the IETS HASAC guidelines were followed for proper embryo handling and treatment. See *Manual of the International Embryo Transfer Society: A Procedural Guide and General Information for the Use of Embryo Transfer Technology Emphasizing Sanitary Procedures* (3rd Edition), D. A. Stringfellow and S. M. Seidel, Editors, IETS, Savoy, Ill., USA, which is herein incorporated by reference in its entirety. Although these procedures exist to reduce or eliminate contamination in oocytes and embryos, which are beneficial to preventing the spread of pathogenic agents, these procedures are not appropriate for use with various other media, such as seminal fluid. First, oocytes have a protective coating, the zona pellucida, which protects the oocytes from the damaging effects of the pathogen reducing or eliminating procedures. Sperm do not have a similar protective coating and thus, may be damaged by the current procedures. Second, oocytes and embryos are relatively large in size (typically on the order of 100 micrometers in diameter) which allows such entities to be handled individually and treated (or "dipped") in a decontamination solution. In contrast, sperm cannot be handled individually because of size limitations (the diameter of sperm heads are typically less than 5 micrometers).

Therefore, it would be desirable to provide a process and an apparatus which would enable one to remove a biological or non-biological sample pellet directly from a tube containing a sample including the pellet and additional media, without disturbing the surrounding media. More specifically, it would be desirable to provide a process and apparatus to allow pathogenic agents such as viruses, bacteria, and other microorganisms to be removed from seminal fluid samples which did not result in damage to the sperm and allowed the sperm to be extracted with a reduced or eliminated risk of re-contamination by contact between the sperm and the pathogenic agents.

SUMMARY OF THE INVENTION

Accordingly, the present invention is directed to a process and apparatus for decontamination and removal of sample pellets from surrounding media while additionally reducing or eliminating the risk of re-contamination of sample pellets with such media. Such a process and apparatus may be used for various isolation procedures involving several sample types including both biological (i.e. DNA, RNA, or protein) and non-biological samples.

The process and apparatus of the present invention has a wide range of applicability and utility. For instance, an object of the present invention is to provide a process and apparatus by which to reduce contamination in seminal fluid. Such process may be used to decontaminate human semen especially for known sexually transmitted pathogens that are of significant health concern i.e. viruses such as HIV, Hepatitis B and C. As a result, this invention may allow infected men to participate in procedures such as artificial insemination, in vitro fertilization, and other suitable applications in assisted reproductive technology without transmitting such infectious agents to their spouses, unborn children or to health care workers handling the contaminated semen samples.

This invention may also be used in animal or livestock industries. The potential exists to infect both a fetus and a mother through pathogen-infected sperm. Recently, the threat of pathogenic agents being transported internationally has impacted the ability to import sperm cells. In livestock, the foot-and-mouth disease virus and porcine reproductive and respiratory syndrome (PRRS) virus have shown to have devastating consequences to the national and international agricultural economies. As a result of such disease outbreaks, stricter regulations and sometimes bans on importation of animals or semen have been enacted which, in turn, affect animal and livestock industries by cutting off supplies and sources of new genetic materials.

The present invention, which reduces or eliminates pathogenic agents from seminal fluid, may allow such seminal fluid to be safely transported around the world. This is in light of the precedent set by the trypsin treatment procedure for processing embryos. Trypsin treatment of embryos has shown that the risk of transmitting specific infectious agents by embryo transfer is minimal if the embryos are properly treated. Consequently, regulatory restrictions for the international transport of livestock (mostly cattle) embryos by certain entities (e.g., USDA) have been reduced.

By allowing international transport, the present invention may give zoos and conservation projects the opportunity to import sperm from other countries with the reassurance that the risk of receiving seminal fluid contaminated with pathogenic agents is reduced or eliminated. This may help diversity and conservation of animal life—which include the germplasm of rare and/or endangered livestock breeds for germplasm banking programs throughout the world, including the United States (e.g., USDA Agricultural Research Services, National Animal Germplasm Program).

The present invention addresses the aforementioned problems by identifying a new and successful apparatus and process for the decontamination of biological and non-biological samples, such as seminal fluid. The process does not damage the sperm acrosome and thus, the sperm cells remain functional. This invention may be useful in a variety of applications such as decontamination of seminal fluid for propagation of livestock, international animal semen transport and other similar animal applications. In addition, the invention may be useful in decontamination of human semen containing known sexually transmitted pathogens which are of great health concern, including viruses such as HIV, Hepatitis B and C, as well as other pathogens. Therefore, the present invention which provides a successful process to decontaminate seminal fluid has significant implications for humans, livestock, zoo animals and wildlife.

In general, samples (i.e., seminal fluids) are processed by use of an apparatus which includes a receiving cylinder having a drain, which allows the fluids to decant slowly down the side of a tube, such as a standard test tube. The apparatus also includes an aspiration channel that allows direct removal of the sample pellet without first removing the surrounding media or disturbing the sample media. The aspiration channel provides a passageway, through the surrounding media, to the sample pellet. An aspiration device, such as a modified micropipette tip, which allows for the aspiration of the sample pellet, is inserted through the aspiration channel into the location of the sample pellet. Therefore, samples are prepared, subjected to centrifugation, and then, sample pellets are removed by aspiration.

More specifically, the present invention is directed to a process for decontamination of biological samples, including seminal fluid, such as through the use of a two-step decontamination method. First, the seminal fluid is incubated in a novel antibiotic cocktail capable of decontaminating a variety of microorganisms, including bacteria. Second, upon placement within the novel apparatus of the present invention, the sperm are subjected to gentle centrifugation resulting in a pellet of decontaminated sperm cells.

The present invention is further directed to a process by which contaminating viruses are removed from seminal fluid by centrifugation of the fluid through a multi-layered gradient, such as a coated silica particle gradient, to obtain a pellet of decontaminated sperm cells; gradients may include an enzyme and an enzyme inhibitor. The process inactivates free viruses and removes somatic cells present in the seminal fluid that may contain viruses.

In one embodiment of the present invention, a gradient of silica particles coated with either polyvinylpyrrolidone or silane is utilized. The semen sample first passes through a layer containing active trypsin and then, into a second layer containing a soy-based trypsin inactivator when subjected to gentle centrifugation (700×g for 30 min). Several advantages are associated with utilizing this method: (1) sperm are protected from damage by being subjected only briefly to trypsin; (2) free infectious agents that are associated with or adhering to the sperm are eliminated by trypsin exposure; (3) dead and/or damaged sperm are separated from viable, treated sperm; and (4) somatic cells (which can contain pathogenic agents) are separated and removed from the treated, viable sperm because such cells do not pass into the final gradient when subjected to low-speed centrifugation (live sperm do pass through because of their progressive forward motility).

There are currently no known processes that combine a density gradient centrifugation system with an enzyme treatment to decontaminate sperm. Furthermore, there are currently no products available that would allow direct access to and removal of the treated sperm sample pellet (which is on the bottom of a tube containing the multiple gradients) without passing the treated sperm through the upper and potentially contaminating layers.

The current techniques for isolating samples following any decontamination procedure are inherently flawed because of the likelihood of transferring infectious agents back to the treated sperm sample (e.g., directly from the pipette or indirectly from contaminates running down the side of the tube during aspiration). An important feature of this invention, therefore, is the design of a novel mechanical assembly utilizing novel mechanical components, such as plastic-ware, that will facilitate: (1) the layering of the density gradients and semen; (2) treatment of the semen; (3) isolation of the treated sperm from the contaminated material and (4) extraction of the treated sperm and reduction or elimination of the risk of the treated sperm being re-contaminated by the pathogenic agents.

The Certified Semen Services (CSS), a wholly owned subsidiary of the National Association of Animal Breeders (NAAB), established a method for bacteria decontamination in semen. That process is greatly improved upon in this invention which utilizes a novel treatment technique, a novel mechanical assembly, and novel agents for treatment.

First, with respect to the novel agents employed for treatment, the present invention uses a higher concentration of antibiotics as well as an additional antibiotic both of which increase the effectiveness of the antibiotic cocktail to inactivate bacteria and other susceptible microorganisms.

Second, with respect to the novel treatment techniques, these antibiotics are established in a novel gradient pattern to further increase the effectiveness of the present invention for inactivating bacteria and other susceptible organisms. Further, the novel technique increases the amount of time and the temperature at which the semen sample is treated with the antibiotic cocktail. The currently utilized CSS decontamination procedure allowed the semen sample to be exposed to the antibiotic cocktail for three to five minutes at room temperature. The effectiveness of this decontamination process is questionable because decreased temperature causes decreases in bacteria metabolism and thus, antibiotic reaction. Further, the extremely short exposure time (3-5 min) of the bacteria to the antibiotic is also likely not sufficient because it takes longer than such time period for bacteria to divide (the time when the antibiotics exert their effects). Therefore, the present invention alleviates this problem, in an embodiment, by incubating semen in the novel antibiotic cocktail solution for a minimum of 2 hours at physiological temperature. By increasing both the duration of antibiotic treatment and temperature, the metabolism of the bacteria and the subsequent inactivation should be more effective and more useful.

Finally, the present invention employs a novel mechanical assembly within which the novel antibiotic gradient is established and the novel treatment techniques are performed. The mechanical assembly further provides for the separation of the sample pellet from the bacteria and other susceptible agents and allows for the removal/extraction of the sample pellet while reducing or eliminating the risk of re-contaminating the sample pellet through contact with the bacteria and other susceptible agents.

It is to be understood that both the forgoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which:

FIG. 6A is a side view illustrating a tube of the present invention in which a density gradient is utilized, the gradient including 0.125% trypsin;

FIG. 11A is an illustration of an insert receptacle provided as a kit that includes a sterilized package for housing;

FIG. 11B illustrates the insert receptacle including a view of the insert receptacle connected within a tube;

FIG. 15 is a table illustrating a relationship between decreasing concentrations of soy-based trypsin inactivator and detachment of confluent BRL monolayers;

DETAILED DESCRIPTION OF THE INVENTION

Reference will now be made in detail to the presently preferred embodiments of the invention, examples of which are illustrated in the accompanying drawings.

Figure 1:
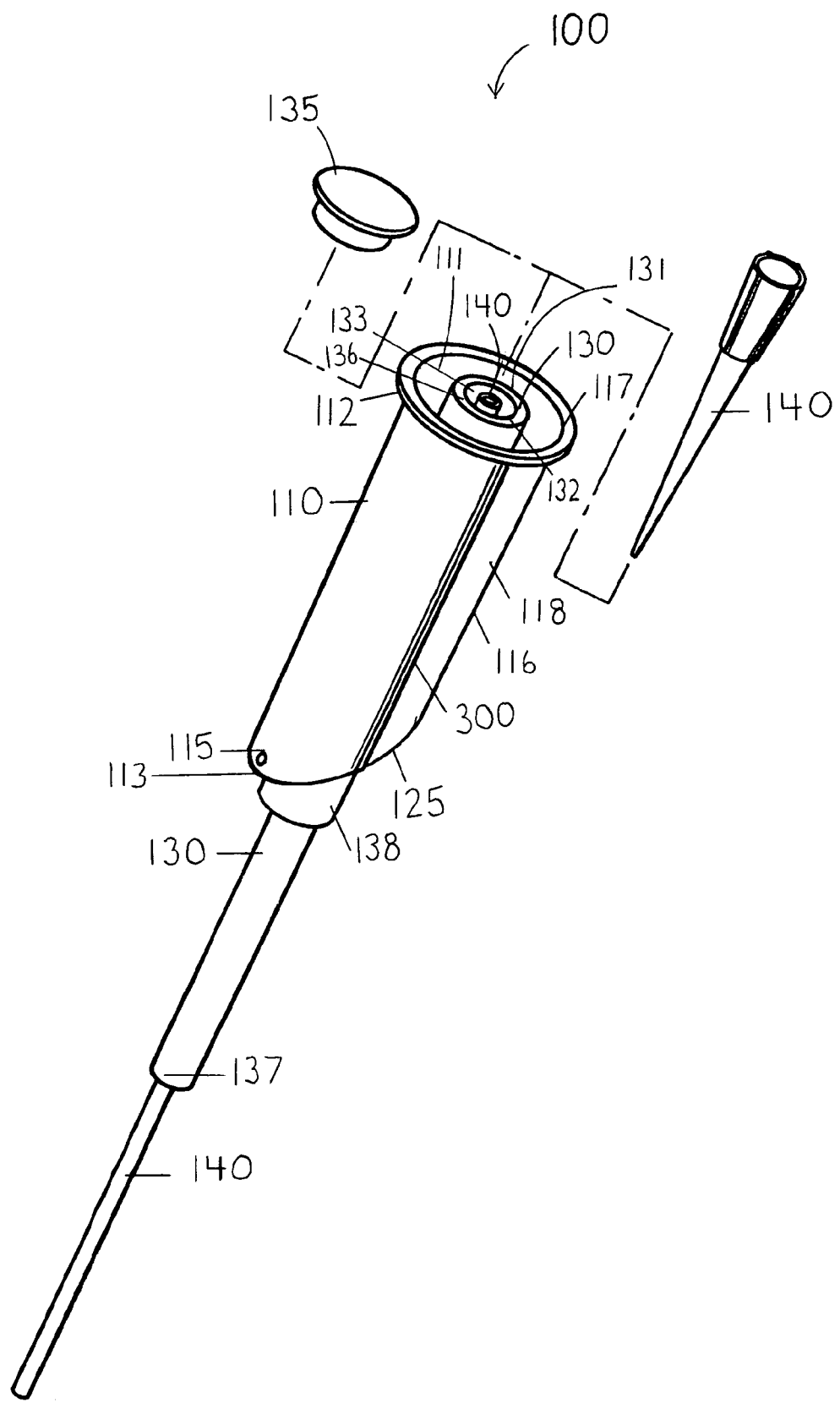
FIG. 1 is an isometric illustration of an insert receptacle in accordance with an exemplary embodiment of the present invention.
Figure 2:
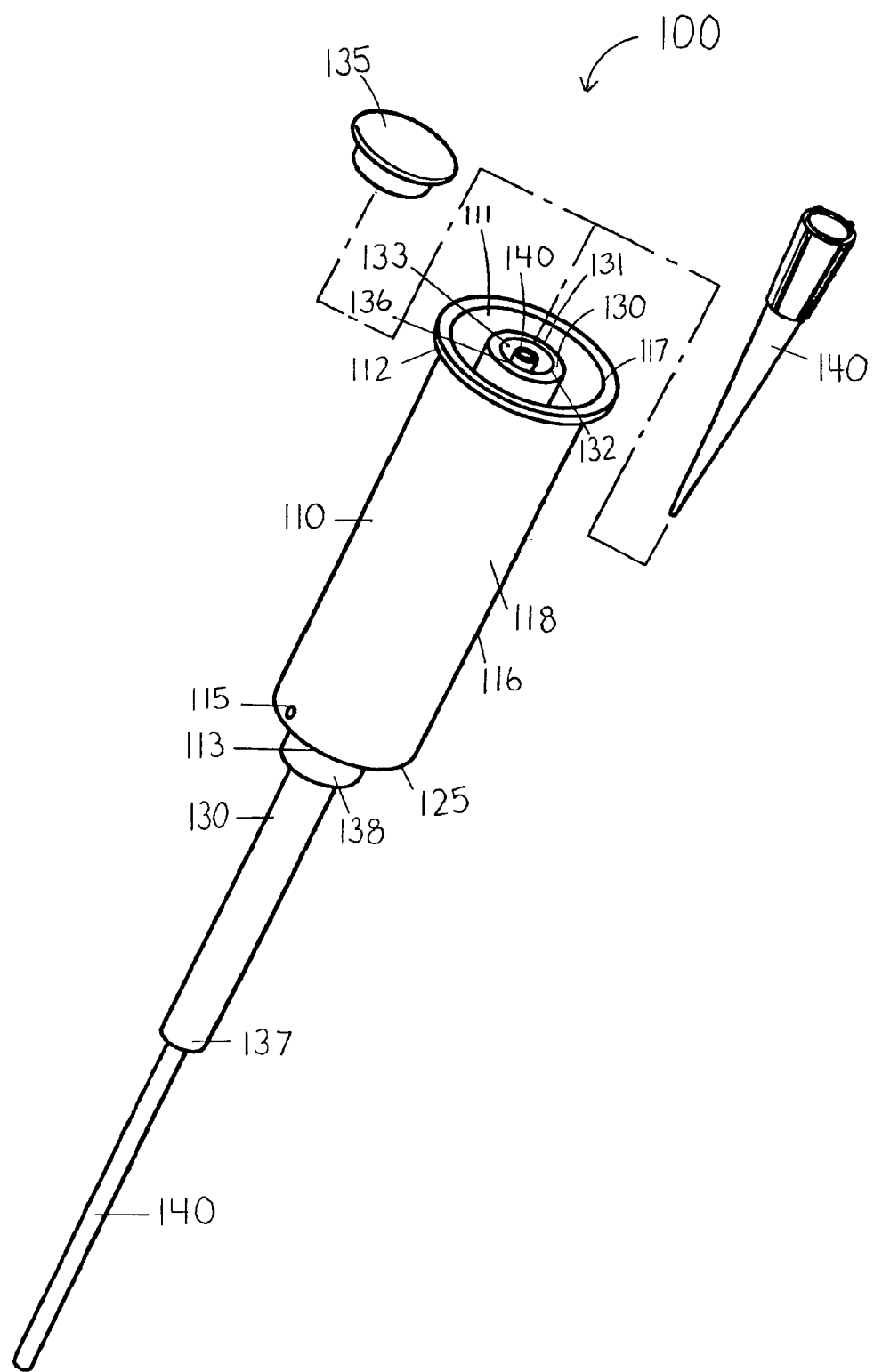
FIG. 2 is an isometric view illustrating a second exemplary embodiment of an insert receptacle of the present invention.
Figure 3:
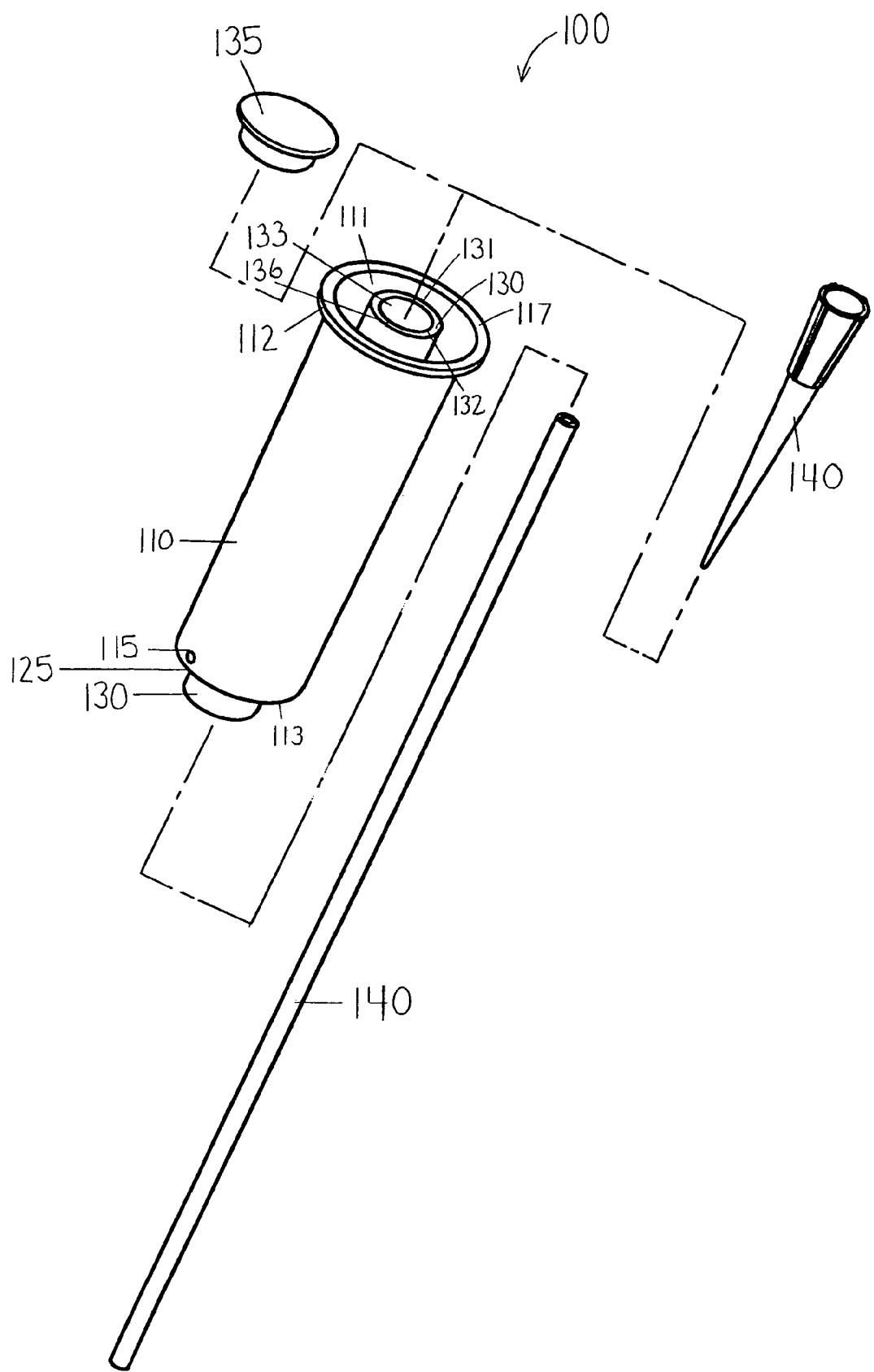
FIG. 3 is an exploded view illustrating the insert receptacle of FIG. 2.

Referring generally now to FIGS. 1 through 17, exemplary embodiments of the present invention are illustrated. In FIGS. 1, 2, and 3, exemplary embodiments of an insert receptacle 100 are shown. The insert receptacle 100 includes a receiving cylinder 110 and an aspiration channel 130. The receiving cylinder 110 further includes a drain 115 and a floor 125. The aspiration channel 130 is capable of connecting with a cap 135 or receiving, through the channel, an aspiration device 140, such as an elongated micropipette tip. In a preferred embodiment, the insert receptacle 100 is constructed to fit securely inside a tube 200, such as a standard (polystyrene) test tube or the like, as shown in FIGS. 6B, 7, 11B, and 12. The insert receptacle 100 connected with the tube 200 forms a decontamination device 400. The insert receptacle 100 is used to form a sample in the bottom of the tube 200 and then, through use of the aspiration device, to extract that sample by aspiration.

The receiving cylinder 110 defines a recessed chamber 111 extending from a first "top" end 112 to a second "bottom" end 113. In the current embodiment, the floor 125 establishes the second end 113. The chamber 111 is constructed for easily receiving a biological or non-biological sample, such as seminal fluids, within. A cylindrical wall 116 includes an inner wall 117 which defines the diameter of the chamber 111 and an outer wall 118 which defines the outer diameter of the receiving cylinder 110. In a preferred embodiment, the receiving cylinder 110 is generally cylindrical, with the top end 112 being open to an environment and the second end 113 being closed.

The drain 115 is an opening that allows samples, such as seminal fluids, to pass through the receiving cylinder 110 and into the tube 200, when the decontamination device 400 is being utilized. In the embodiment illustrated in FIGS. 1 through 3, the drain 115 is a generally circular opening located at the lowest point of the second end 113 or floor 125 and is approximately one millimeter in diameter. However, the drain 115 may be of various sizes, such as less than one millimeter and greater than one millimeter, to accommodate fluids of different viscosities. For instance, the drain 115 may be 2 millimeters, 3 millimeters, 4 millimeters, 5 millimeters, or the like. In an alternative embodiment, the drain 115 is funnel shaped to enhance the efficient, but slow release of sample, i.e., fluid, into the tube 200.

The floor 125 of the receiving cylinder 110 may be constructed in a variety of configurations. For example, in the embodiment illustrated in FIG. 1, the floor 125 is an angled floor, which facilitates fluids in passing through the recessed chamber 111 of the receiving cylinder 110 and into the tube 200. In the embodiment illustrated in FIGS. 2 and 3, the floor 125 is substantially planar (flat). In further embodiments, the floor 125 has a generally concave or convex shape. In embodiments where the floor 125 is planar (flat) or concaved, the floor 125 may be constructed as an internal ramp to guide fluids to the drain 115.

It is to be understood that the floor 125 may be constructed somewhere between the first end 112 and second end 113 of the receiving cylinder 110. The floor 125, in such an embodiment, may be configured in a similar manner and provide similar functional capabilities as described previously and further discussed below. The drain 115 is constructed to provide for the passage of the samples from the floor 125 to the tube 200, therefore, the drain 115 may include an extended shaft which runs from the floor 125 through the cylindrical wall 116. The drain may be variously positioned along the outer wall 118, to provide for the decanting of the sample into the tube 200, described below.

The aspiration channel 130 is a generally cylindrical tube which extends from the top end 112 through the bottom end 113 of the receiving cylinder 110. It is to be understood that the shape of the aspiration channel 130 may be varied. For instance, the aspiration channel 130 may be constructed in a generally rectangular shape or various polygonal shapes which assist in promoting removal of sample pellets and prevention of re-contamination. The aspiration channel 130 is positioned in a substantially centerline location of the receiving cylinder 110. It is contemplated that the aspiration channel 130 may be located off-set from the centerline of the receiving cylinder 110. The location of the aspiration channel 130 may be varied in order to increase the effective transfer of fluid from the receiving cylinder 110 to the tube 200 and removal of sample pellet from the tube 200.

In the current embodiment, the aspiration channel 130 extends from the bottom end 113, or floor 125, of the receiving cylinder 110. For example, the aspiration channel 130 may extend from the bottom end 113 down to a pre-determined mark, such as a 0.5 mL mark, on the tube 200, as shown in FIG. 11B. The length of the aspiration channel 130 may vary to provide the aspirating functionality it is designed for, which is to guide the aspiration device down through the receiving cylinder 110 into the biological sample at the bottom of the tube 200.

In a preferred embodiment, the aspiration channel 130 is an integral part of the receiving cylinder 110. An outer wall 131 of the aspiration channel 130 limits and defines further the recess chamber 111 of the receiving cylinder 110. An inner wall 132 of the aspiration channel 130 defines a hollow 133, which runs the length of the aspiration channel 130, and receives an aspiration device 140 within. A first "top" end 136 of the aspiration channel 130 is flush with the top end 112 of the receiving cylinder 110. The aspiration channel 130 is connected through the bottom end 113 and/or floor 125 of the receiving cylinder 110. In the integral embodiment herein described, a section of the outer wall 131 connects with and through the bottom end 113 and a second end 137 of the aspiration channel 130 is extended below the bottom end 113. It is contemplated that the second end 137 of the aspiration channel 130 may simply connect with the bottom end 113 and/or floor 125, establishing the channel through the bottom end 113 and/or floor 125.

In an alternative embodiment, the aspiration channel 130 is a removable component of the insert receptacle 100. In this embodiment the aspiration channel 130 is removable from the receiving cylinder 110. In order to enable this removable functionality the bottom end 113 and/or floor 125 of the receiving cylinder 110 includes a port 138. The port 138 being an opening located in the bottom end 113 and/or floor 125 so that the aspiration channel 130 can connect with the port 138 and pass through the bottom end 113 and/or floor 125. In the embodiments illustrated in FIGS. 1 through 3, the port 138 is a circular shaft and of a diameter slightly larger than the outer diameter of the aspiration channel 130. This prevents fluids from leaking through the port 138 and down the outer wall 131 of the aspiration channel 130. It is contemplated that an additional device for strengthening the seal between the port 138 and the aspiration channel 130, such as a rubber gasket, a plastic O-ring, or the like, may be employed.

As previously stated, the aspiration channel 130 connects with a cap 135. The cap 135 is primarily utilized when the receiving cylinder 110 is being filled with the biological sample, such as seminal fluids. The cap 135 provides a seal for the top end 136 of the aspiration channel 130. In a preferred embodiment, at least a section of the cap 135 fits inside the aspiration channel 130 sealing off the top end 136. In an alternative embodiment, the cap 135 is a plastic sticker that connects, over the top end 136, to the aspiration channel 130 through use of an adhesive. The cap 135 also functions to assist in preventing contamination of the biological sample by providing a barrier which may prevent fluids from falling down the aspiration channel 130. The cap 135 is removable so that the aspiration device 140 can be inserted into and through the aspiration channel 130.

The inner diameter of the aspiration channel 130, established by the inner wall 132, is of suitable dimensions for accepting/receiving the aspiration device 140 within. Allowing the aspiration device 140 to fit within the aspiration channel 130 is of critical importance for the removal/extraction of a biological pellet from the tube 200, which is discussed in detail below.

It is contemplated that the overall shape of the receiving cylinder 110 and aspiration channel 130 may vary to provide for the removal of pathogen and extraction of pellet functionality which is described below. In the exemplary embodiments, the overall shape is generally cylindrical. However, it is contemplated that the overall shape may be substantially square, rectangular, or various other polygonal configurations.

In the current embodiment, the aspiration device 140 is an elongated micropipette tip that the user couples with a suction device, such as a standard syringe. The aspiration device 140 connected with the syringe provides for pulling/aspirating the sample pellet through and from the tube 200. The aspiration device 140 is configured to be received within the aspiration channel 130 and as such generally conforms to the shape of the aspiration channel 130. However, it is contemplated that the aspiration device 140 may be variously configured, such as in various polygonal configurations, which may promote its extension through the aspiration channel 130 and extraction of the sample pellet from the tube 200.

The outer wall 118 of the cylindrical wall 116 may be equipped with a connection assembly 300 for securely affixing the insert receptacle 100 within a section of the tube 200, as shown throughout the drawing figures of the present invention. The connection assembly 300 may be a variety of mechanical connection assemblies such as a compression lock assembly, a latch assembly, a snap-fit assembly, or the like. In a preferred embodiment, the connection assembly 300 is a friction fit assembly constructed as a series of protrusions. The series of protrusions may assist in stabilizing and affixing the position of the receiving cylinder 110 against the inner wall of the tube 200. In the embodiment illustrated in FIG. 1, the series of protrusions are vertical ribs of a length equal to the height of the cylindrical wall 116. In other embodiments, the vertical ribs are of a length less than the height of the cylindrical wall 116. There may be any number of vertical ribs disposed on the cylindrical wall 116 of the receiving cylinder 110. The vertical ribs may be evenly spaced around the cylindrical wall so that air or other gases may pass freely to and from the area of the tube underneath the receiving cylinder 110 and the environment outside the tube 200. In an alternative embodiment, the series of protrusions are circumferential ribs that circle the receiving cylinder 110. The circumferential ribs are constructed to provide air channels which allow for the passage of air or other gases to and from inside the tube and an outside environment. The circumferential ribs may be evenly spaced around the cylinder wall 116 or may be constructed in a staggered pattern about the cylindrical wall 116. The air channels are notches cut out of the circumferential ribs so that the circumferential ribs are prevented from acting as an airtight seal against the tube 200. In another embodiment, the series of protrusions are helical ridges, which may allow the insert receptacle to be twisted into the tube 200, like a screw. The helical ridges are also equipped with air channels for allowing air pressure to equalize between the tube 200 and the outside environment. In yet another embodiment, the series of protrusions are a series of bumps positioned around the cylinder wall 116. It is to be understood that the number, location, and configuration of the circumferential ribs, helical ridges, and the series of bumps may vary to provide for the equalization of pressure between the tube and an outside environment.

The connection assembly 300 is configured to allow air and/or other gases to pass between the receiving cylinder 110 and the tube 200 and out into the outside environment. This prevents the sample from experiencing a bubbling affect or tidal shifts as the sample is aspirated. The bubbling affect is the result of a vacuum, or area of low-pressure air, that is created in the tube 200 due to the volume of sample decreasing during aspiration. The vacuum occurs in the area of the tube 200 below the receiving cylinder 110 and above the uppermost level of the fluid. Bubbling occurs as the pressure abruptly equalizes from the aspirating device being removed from the aspiration channel 130. To further explain, when the aspiration device 140 is removed or is smaller in diameter than the aspiration channel 130, air from outside the tube is allowed to enter the aspiration channel 130, pass through the fluid, and finally bubble up to the area of low-pressure air above the fluid. The bubbling affect is detrimental to the method and apparatus of the present invention because the layers of fluid could mix, causing the sample to be contaminated.

In addition to presenting the decontamination device 400, including the insert receptacle 110 and the tube 200, the present invention also identifies a new and successful method to decontaminate seminal fluid. The method does not damage the sperm acrosome and thus, the sperm cells remain functional. This invention may be useful in a variety of applications such as the decontamination of seminal fluid for propagation of livestock, international animal semen transport, and other similar animal applications. In addition, the invention may be useful for the decontamination of human semen containing known sexually transmitted pathogens which are of great health concern, including viruses such as HIV, Hepatitis B and C, as well as other pathogens. Therefore, the present invention which provides a successful method to decontaminate seminal fluid has significant implications for humans, livestock, zoo animals, and wildlife.

Figure 4:
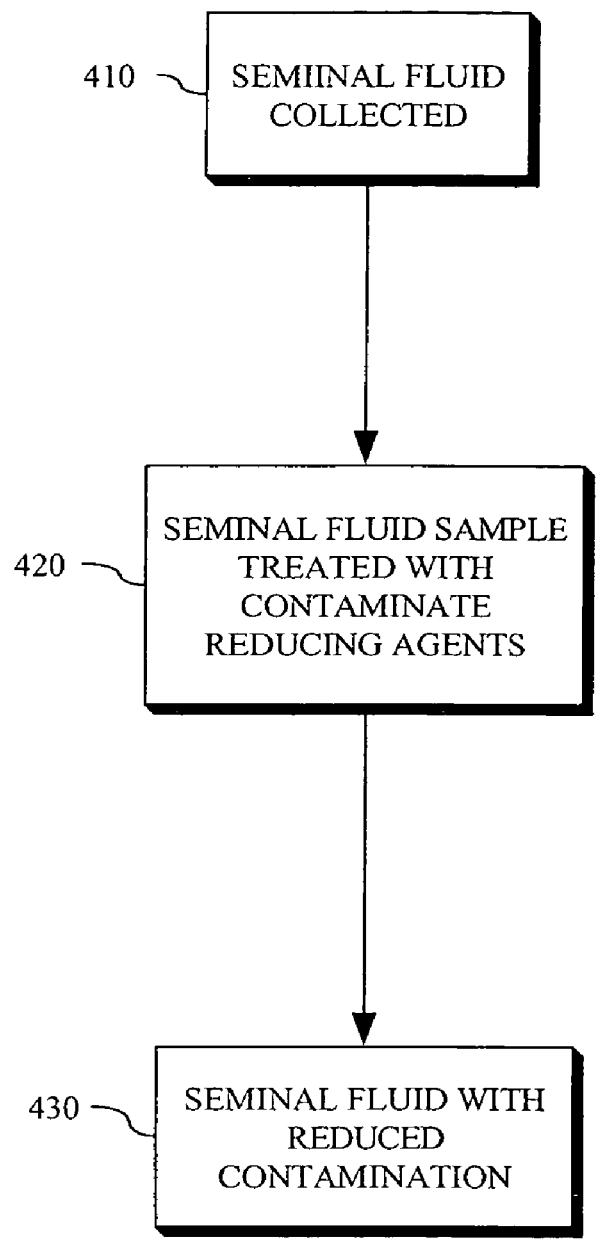
FIG. 4 is a block diagram illustrating an exemplary method of the present invention wherein seminal fluid is decontaminated.

In FIG. 4, an exemplary method of decontaminating a seminal fluid is provided. In a first step 410 a seminal fluid sample (biological sample) is collected. The seminal fluid is treated with contaminate reducing agents (decontamination reagents), such as trypsin, and the like, in step 420. In step 430, these decontamination reagents effectively inactivate contaminate(s)/pathogen(s) and allow the sperm to remain functional, providing a sperm sample with reduced or eliminated contamination. The invention is not limited to the trypsin reagent described, various decontamination reagents may be utilized which effectively inactivate contaminants of various pathogenic agents.

Figure 5A:
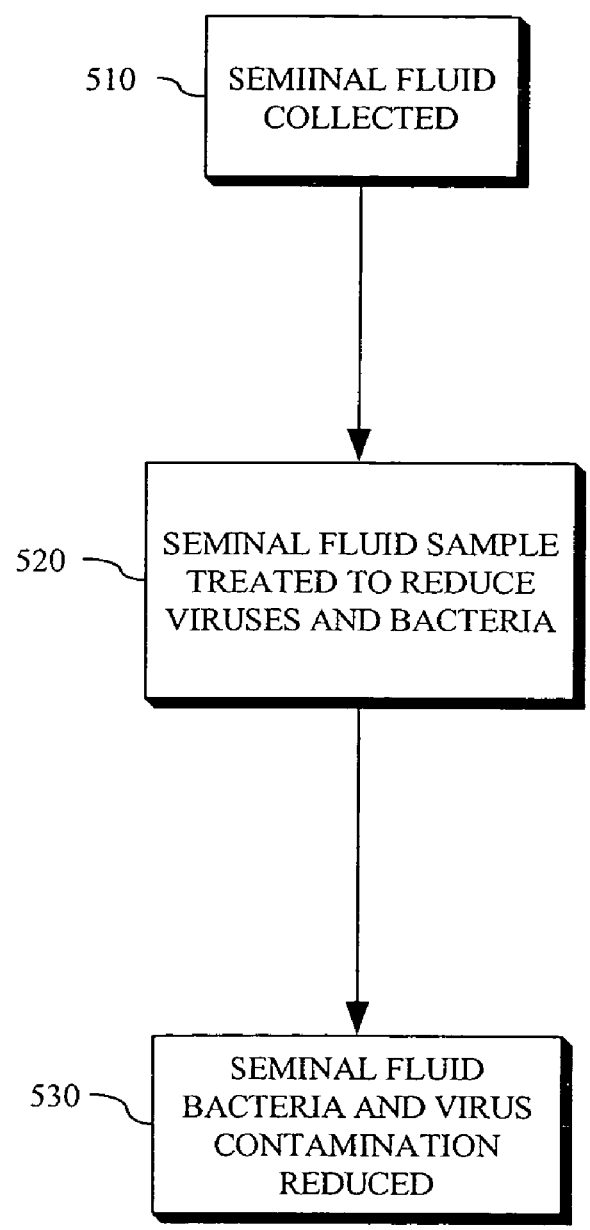
FIG. 5A is a block diagram illustrating an exemplary method of the present invention wherein seminal fluid is treated to reduce viruses and bacteria.

In a further method of the present invention, shown in FIG. 5A, a biological sample (seminal fluid) is collected in step 510. In a second step 520 the seminal fluid is treated with contaminate reducing agents which effectively inactivate bacteria and virus pathogenic agents. The step of treating the seminal fluid with the virus and bacteria reducing agents, as identified in step 520, may be repeated more than once. It is contemplated that the number of treatments may be determined by the user of the present invention. In step 530 a seminal fluid sample is produced with reduced bacteria and virus contamination. In alternative embodiments, the types and combination of reagents used may vary. For example, the reagents may be used together to complete two functions: (1) bacteria decontamination and (2) virus decontamination. Alternately, either reagent may be used alone.

Figure 5B:
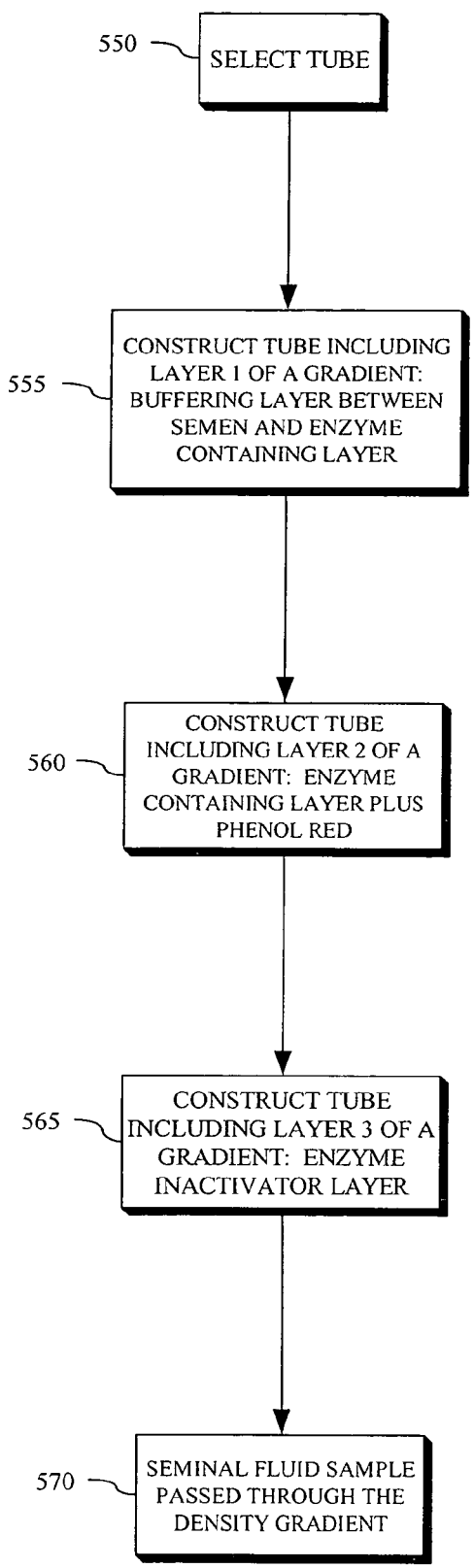
FIG. 5B is a block diagram illustrating an exemplary method of the present invention wherein seminal fluid is decontaminated through use of a gradient including an enzyme.

The present invention may use a mechanical assembly, such as a receptacle, kit, or the like, for providing the method of decontaminating seminal fluid. An exemplary embodiment of the virus decontamination process is shown in FIG. 5B. In a first step 550, a tube, such as tube 200 described previously, is selected. In a second step 555, the tube is constructed with a first layer of a gradient. The first layer of the gradient is constructed as a buffer layer between the seminal fluid sample and an enzyme containing layer. In a third step 560, the tube is constructed with a second layer of the gradient. The second layer is constructed to include an enzyme, such as trypsin, and a marker, such as a phenol red marker. The enzyme inactivates contaminates and the phenol red distinguishes this layer from the other layers. In a fourth step 565, the tube is constructed with a third layer of the gradient. The third layer is constructed of an enzyme inactivator layer. The enzyme inactivator is a soy-based trypsin enzyme inactivator in the current embodiment. The inactivation of the trypsin enzyme provides a sample of motil sperm which has a reduced or eliminated contamination count and does not damage the acrosome of the spermatozoa.

In a fifth step 570, the seminal fluid, which may or may not have been treated with bacteria decontamination agents, passes through (is centrifuged through) the gradient contained in a tube. The gradient may be a density gradient, which has been shown effective for washing human sperm. However, the use of enzymes in the gradient to decontaminate seminal fluid of viruses and/or bacteria is unique and has many unexpected benefits. For instance, the method of decontamination provided by the present invention protects viable sperm, allowing the viable decontaminated sperm to be collected. Further, the present invention allows for decontamination of motile sperm which meets or exceeds safety standards for sperm transport nationally or internationally.

It is contemplated that the present invention provides a method of decontaminating a sample comprising a single step of passing a sample through a density gradient, such as the density gradient described above in reference to FIG. 5B. The density gradient being preferably constructed in a tube, which is connected with an insert receptacle, such as those shown and described previously. It is further contemplated that the present invention provides a method of decontamination which includes a first step of treating the sample with an antibiotic and a second step of passing the sample through a density gradient. In addition, a method of collecting a decontaminated sample pellet may include any combination of the above steps for the above methods and include the step of aspirating the pellet.

Due to the size limitations associated with sperm, sperm could not be individually handled as had been the procedure used previously with samples such as embryos or oocytes. Therefore, a primary achievement of the present invention is a method that allows sperm to be exposed to trypsin for long enough periods of time in order to remove associated pathogens without affecting sperm viability.

Experimental Process and Results

Figure 6B:
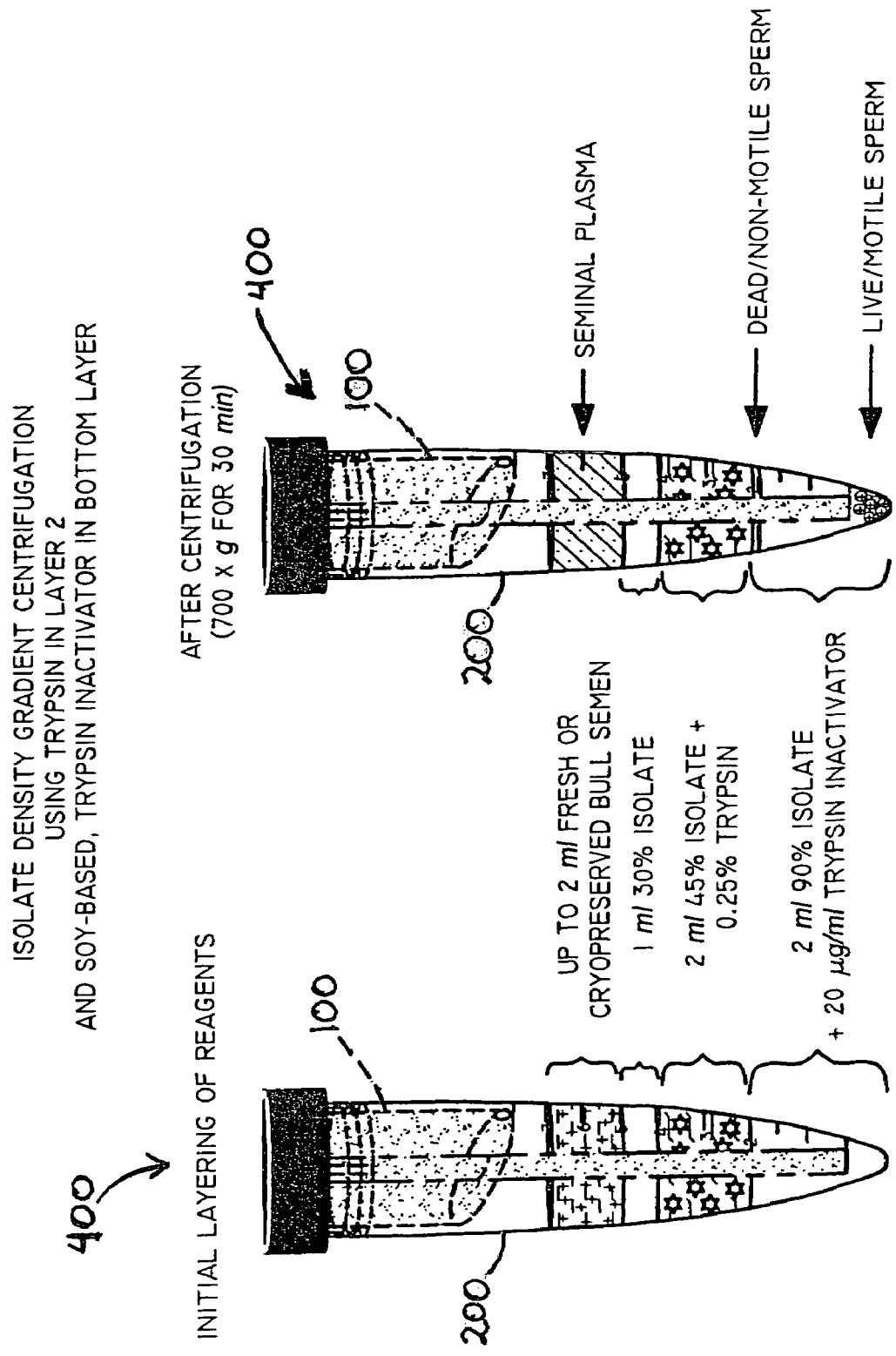
FIG. 6B is a side view illustrating a tube including an insert receptacle of the present invention in which a density gradient is utilized wherein Layer 1 of the gradient serves as a buffering layer, Layer 2 contains 0.25% trypsin, and Layer 3 contains at least 20 µg/ml of trypsin inactivator.

To address this criterion for the treatment of sperm by trypsin, protocols for processing semen were evaluated. As shown in FIG. 6A, the utilization of a density gradient centrifugation procedure which evaluated the effect of varying concentrations of PVP (Percoll)- or (silane Isolate)-coated silica particles and trypsin on sperm viability, was evaluated. A series of experiments were conducted testing the viability of cryostat preserved bovine (*Bos gaurus*) sperm by using a PVP (Percoll) density gradient centrifugation protocol requiring 0.125% trypsin to be added to the middle (45% Percoll) layer, as shown in FIG. 6A. These studies incorporated trypsin at half the concentration recommended for use in embryo decontamination studies (in anticipation of potential detrimental effects to the sperm) and in the absence of a trypsin inhibitor in the bottom (90% Percoll) layer. Subsequent experiments demonstrated no detrimental effects of increasing the concentration of trypsin to 0.25%. As such, 0.25% trypsin was incorporated into the middle layer in the modified protocol, along with the addition of a soy-based trypsin inhibitor (approximately 20 µg/ml) in the bottom layer, as illustrated in FIG. 6B. An additional top layer containing PVP (Percoll)- or silane (Isolate)-coated silica particles was included in the modified protocol in order to serve as a buffer for the semen against the trypsin layer (refer to FIG. 6B). A separate set of experiments were performed to ensure that trypsin was not inactivated after dilution with the PVP-(Percoll) or silane (Isolate)-coated silica particles or after dilution with egg yolk-based cryo-diluents with or without semen. Results established that dilution of trypsin (for final effective concentrations of 0.125% and 0.25%) with any of the aforementioned products did not result in diminished enzymatic activity as determined by the detachment of confluent, somatic cell monolayers after direct exposure to solutions containing various trypsin concentrations (Refer to FIGS. 16 and 17).

Change from PVP-Coated (Percoll) to Silane-Coated (Isolate) Silica Particles

An initial trial was conducted to compare sperm characteristics after application of the semen "disinfection" procedure using PVP (Percoll)-coated silica particles versus Isolate-coated silica particles. The results are summarized in Table 1, below.

TABLE 1

Comparison of Percoll versus Isolate in semen "disinfection" procedure: domestic bull (*Bos taurus*) semen (1 ml) layered on top of 2 ml 45% (Percoll or Isolate) containing 0.25% trypsin over 2 ml 90% (Percoll or Isolate), centrifuged for 30 min at 700 × g then examined at 0 and 2 hours.

| | % Motility | | Kinetic Rating[1] | | % Viability[2] | | % Acrosome Intact[2] | |
|---|---|---|---|---|---|---|---|---|
| | 0 h | 2 h | 0 h | 2 h | 0 h | 2 h | 0 h | 2 h |
| Initial (raw) | 43 | — | 3 | | 70 | — | 70 | — |
| Percoll | 60 | 50* | 2 | 2 | 90 | 41 | 93 | 43 |
| Isolate | 70 | 50 | 2 | 1.5 | 50 | 72 | 50 | 76 |

[1]Rate of forward progression (0 = no movement, to 5 fast, linear progression).
[2]As determined by vital staining (Eosin B/Fast Green).
*Sperm head agglutination observed.

Overall, the presence of Isolate-coated silica particles appeared to result in lower percentages of damaged sperm when compared to those measured in the presence of Percoll-coated silica particles—a greater proportion of acrosome-reacted sperm and increased head agglutination were observed in the Percoll group when compared to the Isolate group after two hours of incubation at room temperature of the treated sperm with the respective reagents.

Figure 7:
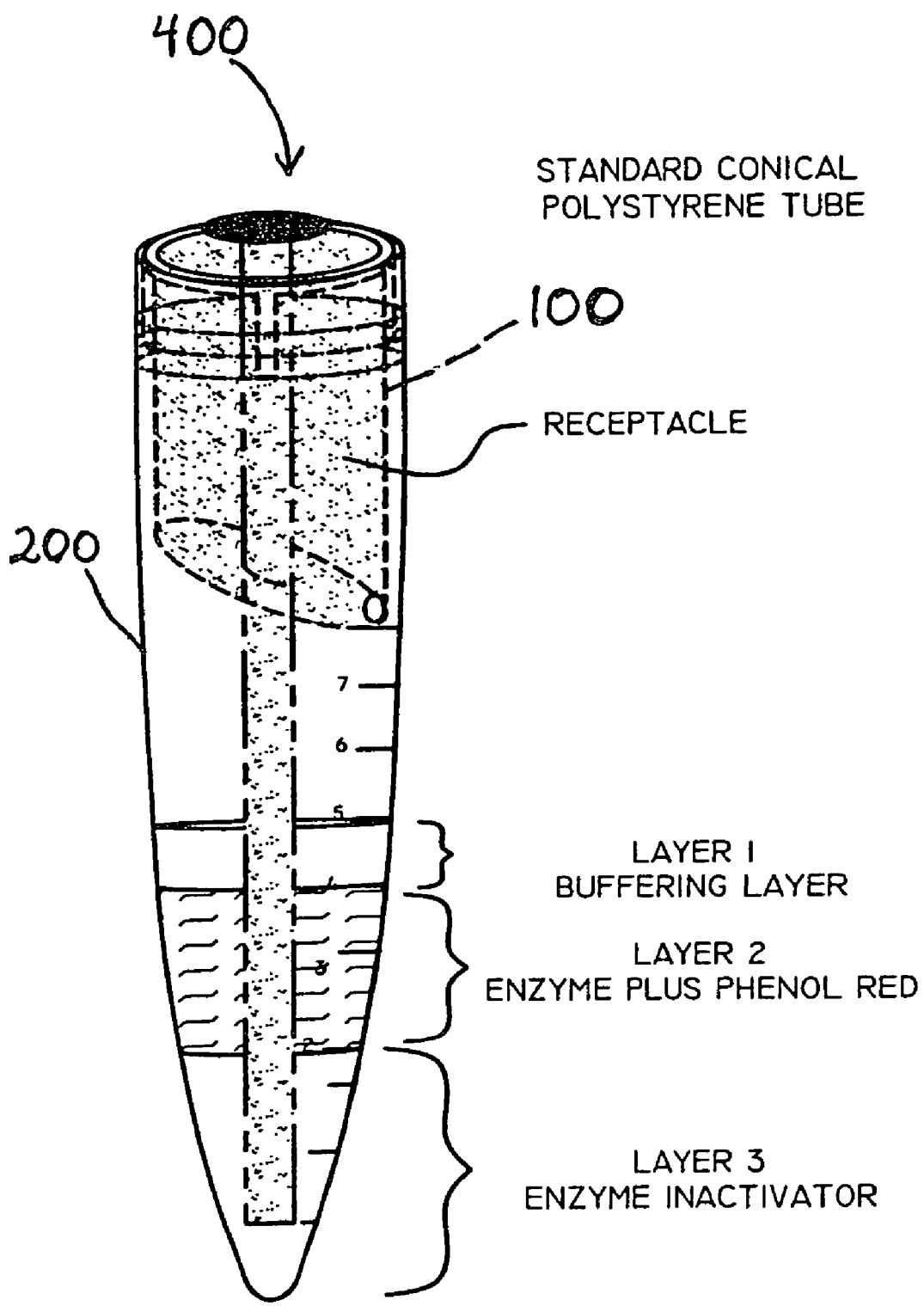
FIG. 7 is an illustration of an insert receptacle engaged within a tube, which may be used to decontaminate seminal fluid and construct the layering effect of the density gradient.

FIG. 7 shows an exemplary embodiment of the decontamination device 400 including the insert receptacle 100 operationally engaged with the tube 200, this construct of the present invention is used for the decontamination of biological samples, such as seminal fluid. In addition, FIG. 7 shows a multi-layered gradient established within the tube 200 and the effect of the gradient. A first layer (Layer 1) includes 1 ml of 30% Isolate. The Isolate preferably composed of a Silane-Coated (Isolate) Silica Particles. However, various other isolates which provide lower percentages of damaged sperm may be used as contemplated by those of ordinary skill in the art. A second layer (Layer 2) contains an enzyme, such as trypsin, and a colorant, such as phenol red which is employed to distinguish the second layer from the other layers. The enzyme used in Layer 2 may be any entity that will be effective in inactivating a virus or bacteria as a pathogenic agent. Further, the colorant in the layer is not limited to phenol red whereby any or no colorant may be employed. Finally, in a third layer (Layer 3) an enzyme inactivator, such as a soy-based trypsin inactivator, may assist in preventing sperm cell damage caused by prolonged exposure to the enzyme in Layer 2 by stopping any reaction that is taking place between the sperm cells and enzyme.

Figure 8:
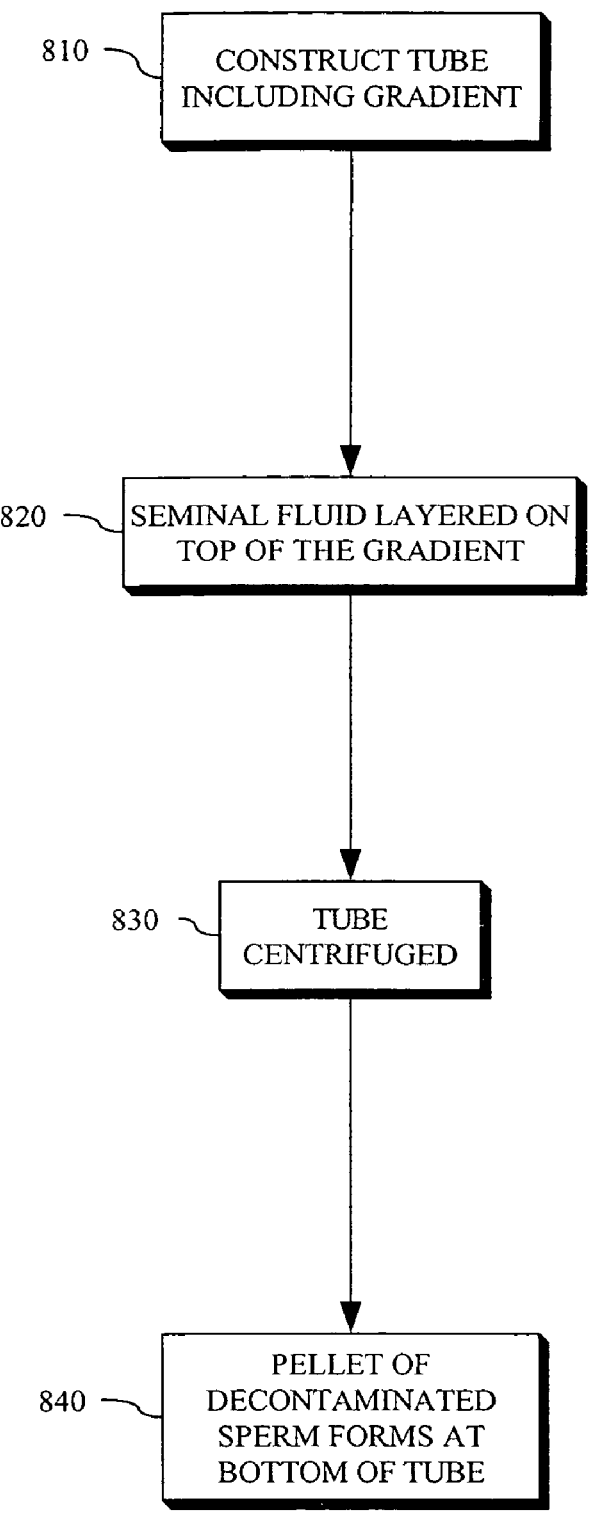
FIG. 8 is a block diagram depicting an exemplary method of the present invention wherein a seminal fluid sample is decontaminated through use of a gradient including an enzyme.

Referring now to FIG. 8, an exemplary method of virus decontamination for a biological sample is shown. In a first step 810 a tube, such as tube 200, is constructed to include a gradient. It is contemplated that the gradient may be similar to that described in reference to FIGS. 6A, 6B, and 7. Alternatively, various gradients may be established utilizing various buffering agents, enzymes, and inactivators as may be contemplated for the decontamination of various pathogenic agents (i.e., bacteria, viruses, etc . . . ) from a sample. In the current embodiment, a first layer (Layer 1) is a buffering layer, which may be composed of buffering agents, such as PVP-Coated (Percoll) and/or Silane-Coated (Isolate) Silica Particles. The buffering agent acting as a barrier between the layered seminal fluid and active enzyme contained in a second layer. Thus, the buffering layer prevents enzymatic activity from occurring upon the spermatozoa contained within the seminal fluid. A second layer (Layer 2) includes an enzyme plus colorant. The enzyme may include various compounds, these compounds may be selected based on their effectiveness at inactivating a desired pathogenic agent from a sample. The colorant is used to distinguish Layer 2 from the other layers. However, it is also contemplated that the colorant may attach with motile spermatozoa, within the seminal fluid, which pass through Layer 2. A third layer (Layer 3) provides an enzyme inactivator. The enzyme inactivator halts enzymatic activity occurring upon the spermatozoa after passing through Layer 2. In a second step 820, a biological sample (seminal fluid) is layered on top of the gradient. In step 830, the tube with the sample and gradient, are centrifuged which causes the seminal fluid to pass through the multiple layers of the gradient. The centrifugal speed and duration of the centrifugal process may vary as contemplated by those of ordinary skill in the relevant art. As a result of the centrifugal process, in step 840 a pellet of the biological sample is formed. The pellet typically has a density which allows it to be isolated at the bottom of the tube.

Figure 9:
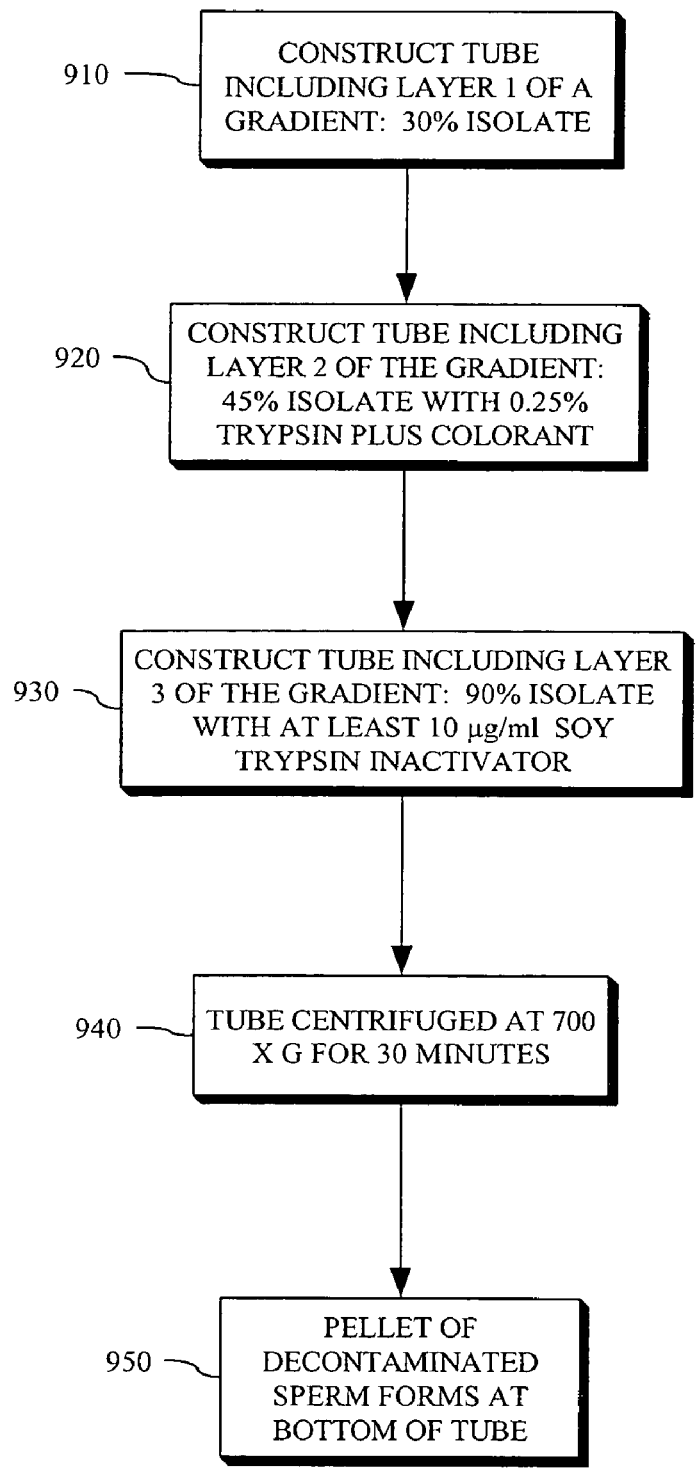
FIG. 9 is a block diagram depicting an exemplary method of seminal fluid decontamination wherein a soy-based trypsin inactivator is employed.

A specific example of the novel decontamination process of the present invention is shown in FIG. 9. In a first step 910 a tube, such as tube 200, is constructed with a first layer (Layer 1) of a gradient, which is a buffering layer composed of 30% Isolate (Silane-Coated Silica Particles). In a second step 920, a second layer (Layer 2) of the gradient is composed of 45% Isolate, 0.25% Trypsin enzyme, and a colorant, such as Phenol Red. Layer 2 is where the enzymatic reactions take place to reduce or eliminate contamination of the seminal fluid by pathogenic agents. In a third step 930, a third layer (Layer 3) of the gradient is composed of 90% Isolate including at least 10 µg/ml of a soy-based Trypsin inactivator. With the tube including the three layer gradient constructed, in step 940 seminal fluid is layered on top of the gradient. In step 950, centrifugation occurs. The tube is centrifuged at 700×g for 30 minutes, which causes the seminal fluid to pass through the multiple layers, resulting in the formation of a pellet of decontaminated sperm cells at the bottom of the tube. Although centrifugation is discussed, any process that will cause the seminal fluid to pass through the gradient layers may be used in accordance with the present invention. As a result of the centrifugation process, in step 960 a pellet of the biological sample forms and isolates at the bottom of the tube.

Figure 10:
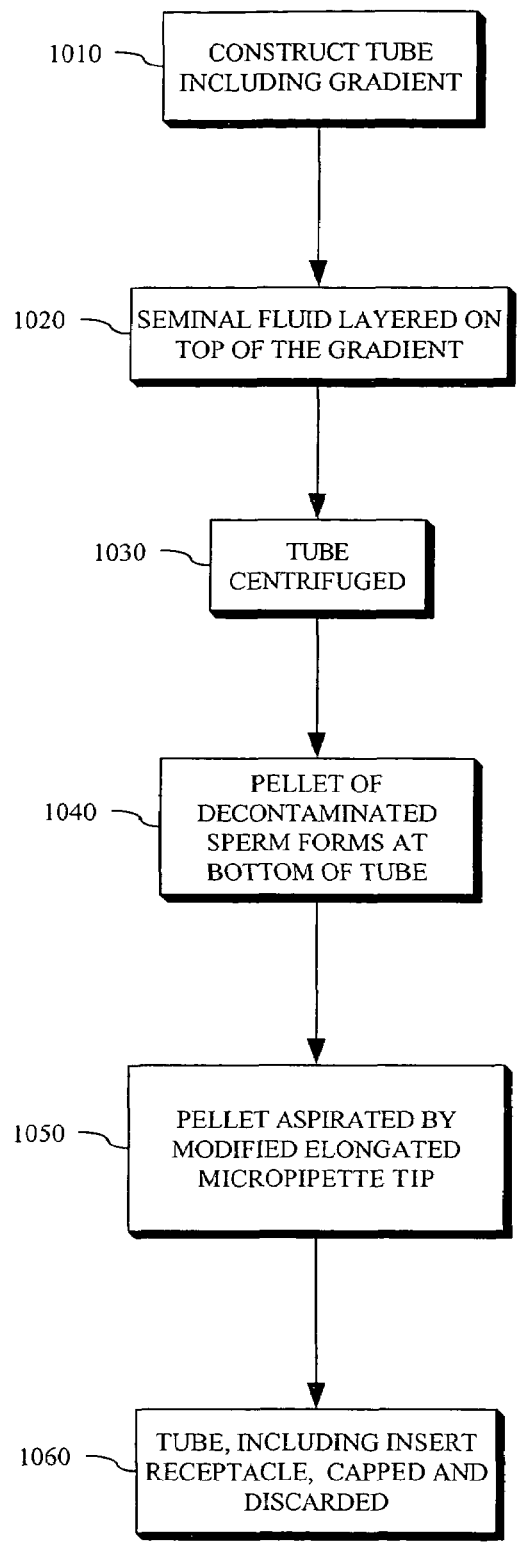
FIG. 10 is a block diagram illustrating an exemplary method of the present invention for decontamination of a seminal fluid and removal of a sample pellet.

FIG. 10 shows a more detailed method of virus decontamination as contemplated by the present invention. In this method the construct of a tube 200 including an insert receptacle 100 is utilized. In a first step 1010 a gradient is established within the tube 200. The gradient is made of Isolate-coated silica particles, however, a suitable preparation device such as Percoll, PureSperm, and the like may also be used. The first "top" layer (Layer 1) of the gradient contains 1 ml of 30% Isolate. The second "middle" layer (Layer 2) contains 1 ml of 45% Isolate including 0.25% trypsin or other suitable enzyme. This layer also contains phenol red or some other colorant to show a visible difference from layer two. However, any or no colorant may be used. The third "bottom" layer (Layer 3) contains 2 ml of 90% Isolate with at least 10 µg/ml of soy trypsin inactivator or other suitable inactivator. A soy-based trypsin inactivator is used because it will not introduce animal pathogens that may be present in animal by-product inactivators. Further, 10 µg/ml of inactivator is the lowest effective concentration of such inactivator which will protect sperm viability. The amounts, percentages, and enzyme used may be changed according to the targeted virus or use.

In a second step 1020 a seminal fluid is layered on top of the gradient. In this step the layering occurs via a decanting of the seminal fluid through a receiving cylinder 110 of the insert receptacle 100, as previously described. This decanting process ensures a slow release of the seminal fluid and may promote better formation of the layer of the seminal fluid on top of the gradient. In step 1030, the entire decontamination device 400, insert receptacle 100 and tube 200, is centrifuged. The decontamination device 400 is centrifuged at 700×g for 30 minutes, which causes the seminal fluid to pass through the multiple layers of the gradient, resulting in the formation of a pellet of decontaminated sperm cells at the bottom of the tube 200. Although centrifugation is discussed, any process that will cause the seminal fluid to pass through the gradient layers may be used in accordance with the present invention. As a result of the centrifugation process, in step 1040 a pellet of the biological sample forms and isolates at the bottom of the tube 200. FIG. 10 continues in step 1050 showing that the pellet is aspirated by a modified, elongated micropipette tip (aspiration device 140). Thus, the sample pellet is removed from the tube 200. By using the modified, elongated micropipette tip, recontamination of the sample pellet by the surrounding media is reduced or eliminated. The tube 200, including the insert receptacle 100, with the remaining contents is then capped and discarded in the biohazardous waste, in step 1060. In additional steps of the present method it is contemplated that the pellet may be stored or gently resuspended in an appropriate solution. Further, the decontaminated sperm may now be used in applications such as artificial insemination, in vitro fertilization, and other suitable applications as are known in the art.

Design of the Decontamination Device Including the Insert Receptacle and Tube for the Isolate/Trypsin Treatment Due to the extreme care which must be taken to ensure that the gradient layers are not mixed during the process and that the resulting pellet is not re-contaminated with surrounding media upon pellet aspiration during the decontamination process, the present decontamination device including the insert receptacle and tube was developed to facilitate such process.

Detailed exemplary drawings of the insert receptacle 100, tube 200, and the decontamination device 400 (insert receptacle 100 plus tube 200) are shown in FIGS. 1, 2, 3, 6A, 6B, 7, 11A and 11B. The plastic used for the insert receptacle 100 and tube 200 is polystyrene and like materials which provide sufficient structural strength to withstand various forces (centrifugal forces) being exerted upon them, allow for the construction of a gradient, and allow for the method of decontamination of a sample, as described throughout the instant application. Polypropylene and like materials are not utilized because such materials may leach toxins that can be detrimental to sperm when incubation occurs for long periods at physiological temperature. Further, the design of the insert receptacle 100 and tube 200 facilitates the maintenance of distinct layers and permits pellet aspiration without risk of re-contamination with surrounding fluids. The measurements (volumes and sizes) listed in the drawing are approximations intended to provide exemplary dimensional characteristics and should not be read as limiting the present invention to these or any other dimensional characteristics. The dimensional characteristics required of the insert receptacle 100 and tube 200 may change due to various reasons, such as the amount of sample, the amount of use, and user preferences, without departing from the spirit and scope of the present invention.

FIG. 11A illustrates a more detailed description of an insert receptacle 100. In the current embodiment, the insert receptacle 100 is constructed as a kit or the like that may be used in the decontamination process. The drawing on the left shows an exemplary embodiment of the components of the insert receptacle 100 as packaged prior to use. The insert receptacle 100, including the aspiration device 140 (modified tip) are packaged and sterilized by gamma radiation. The packaging may be various materials, such as plastic, composite, metal, wood, and the like, which provides a sterile environment within which to store the insert receptacle 100. The drawing on the right notes the positioning of the cap 135, in this instance the cap 135 is a plastic coated "sticker" placed on the top end of the aspiration channel 130 prior to sterilization. Such a sticker is employed to prevent contaminated materials from entering the aspiration channel 130 during gradient formation. Further, it is noted that the aspiration device 140 (modified elongated tip) fits all standard 100 µl micropipettors.

FIG. 11B illustrates a more detailed description of the insert receptacle 100 used in the decontamination process. The drawing on the left shows the insert receptacle 100 made out of polystyrene plastic or like material which consists of two main components—the receiving cylinder 110 and the aspiration channel 130. The receiving cylinder 110, in this current embodiment includes an angled floor 125 through which the aspiration channel 130 protrudes in both directions. Further, a drain 115, which is a small opening through the cylinder wall 116 operationally connected to the floor 125 assures fluids decant slowly down the side of the tube 200. A connection assembly 300 includes a series of protrusions or spacers which may assist in positioning the insert receptacle 100 in the center of the tube 200 and ensuring a tight fit of the insert receptacle 100 in the tube 200. The drawing on the right illustrates an example of the insert receptacle 100 in operational contact with the tube 200. As noted, in a 15 ml conical tube, the receiving cylinder 110 of the insert receptacle 100 fits to the 8 ml mark of the tube 200 while the aspiration channel 120 ends at the 0.5 ml mark on the tube 200.

Figure 11C:
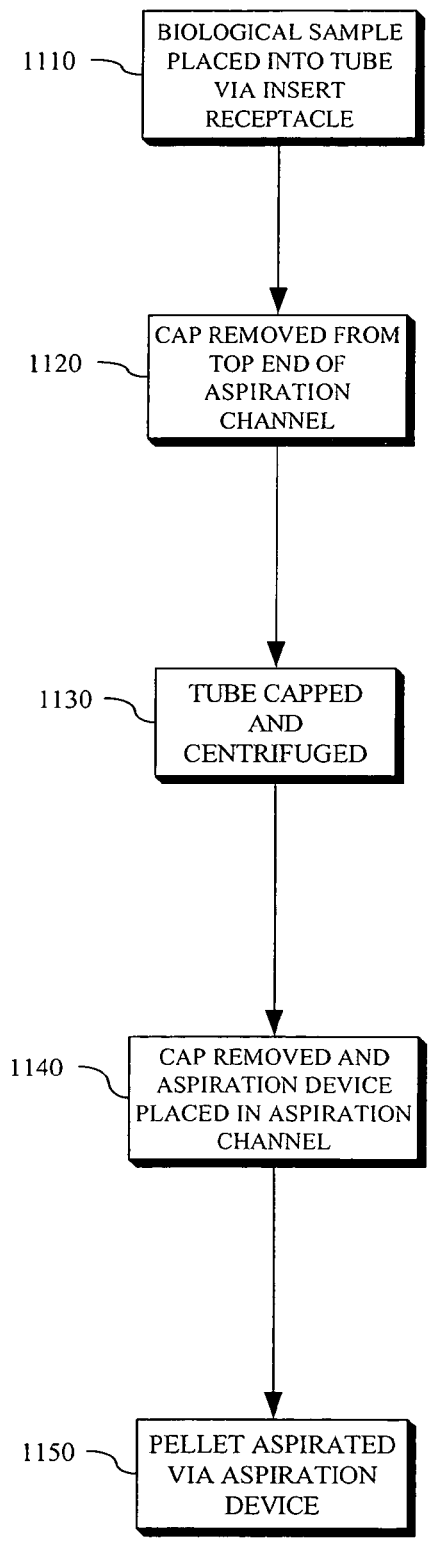
FIG. 11C is a block diagram illustrating an exemplary method of the present invention wherein a sample is processed by use of a tube connected with an insert receptacle including a receiving cylinder, aspiration channel, and aspiration device.

FIG. 11C is a flow chart depicting a method for removal of sample pellets while removing the risk of recontamination of the pellet with surrounding media during pellet isolation. In a first step 1110 a biological sample is placed into a tube 200 (conical polystyrene tube) by pouring said sample into the receiving cylinder 110 of the insert receptacle 100. Said insert receptacle 100 slowly releases the sample through the drain 115 into the tube 200. Once the sample has been completely transferred to the tube 200, in step 1120, the cap 135 (plastic "sticker") on the top end of the aspiration channel 120 is removed. In step 1130 the tube 200 is capped, and then the tube 200, including the insert receptacle 100, is subjected to centrifugation in order to pellet the biological sample. After centrifugation, in step 1140, the cap is removed from the tube 200. Further, an aspiration device 140 (modified micropipette tip) is attached to any standard 100 µl micropipettor. The cap 135 is removed from the aspiration channel 130 and the aspiration device 140 is inserted through the aspiration channel 130 into the bottom of the tube 200 where the sample pellet is located. Once inserted, in step 1150 the aspiration device 140 utilizing the micropipettor aspirates the pellet. The device utilized to pellet the biological sample may be altered without deviating from the scope and spirit of the present invention. Further, it is contemplated that one or more layers of solution may be added to the tube via the receptacle prior to the addition of the biological sample.

Figure 12:
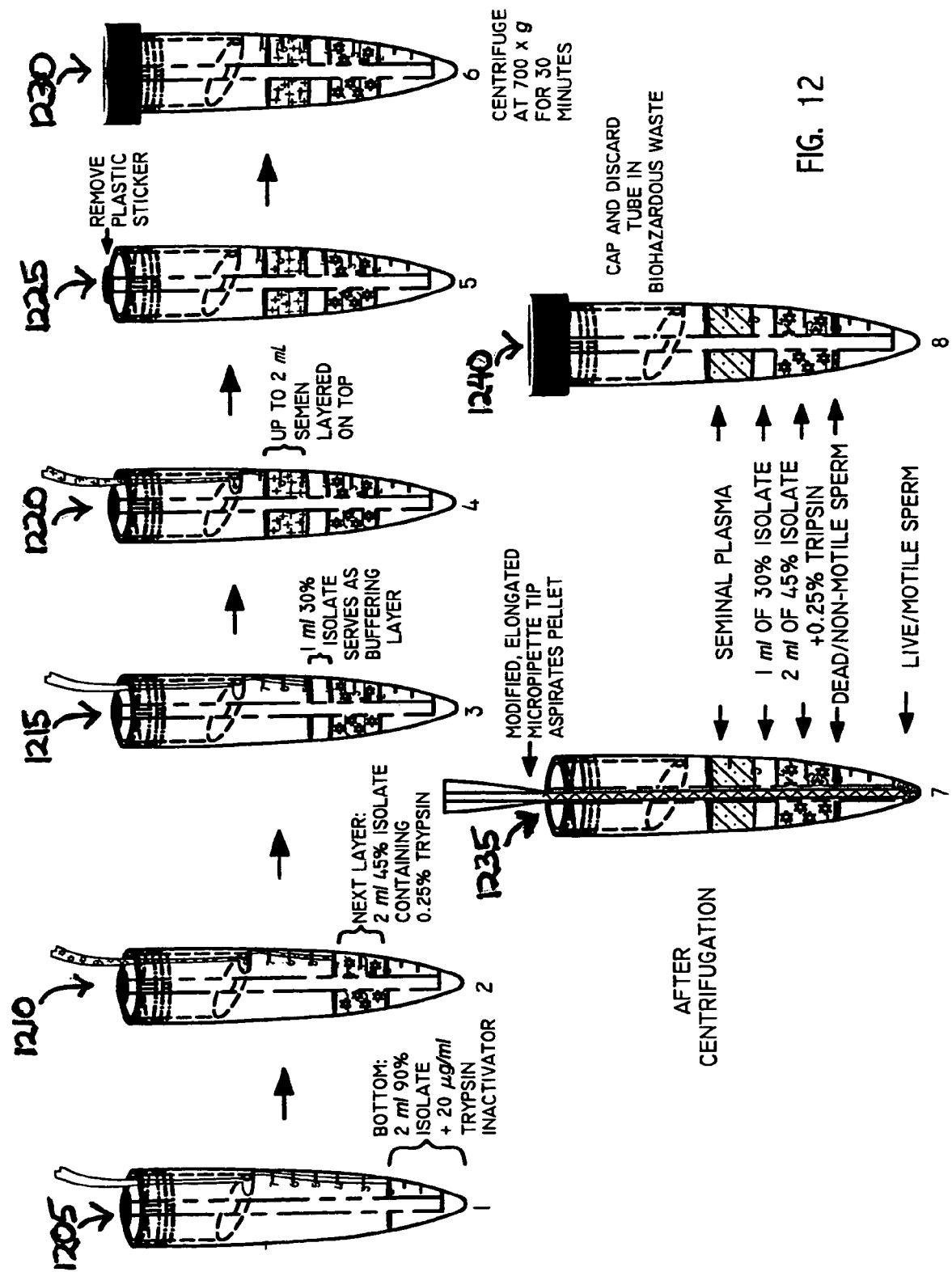
FIG. 12 is a graphical depiction of the step-by-step method for the decontamination of a seminal fluid and removal of a sperm sample pellet.

FIG. 12 graphically depicts a step-by-step method for decontaminating sperm samples. In a first step 1205, 2 ml of 90% Isolate containing 20 µg/ml soy-based trypsin inactivator is placed into the insert receptacle 100 which slowly releases the fluid through the drain 115 into the bottom of the tube 200. In a second step 1210, 2 ml of 45% Isolate solution containing 0.25% trypsin and phenol red is added to the tube 200, by the same process. In a third step 1215, 1 ml of 30% Isolate solution is added and then in step 1220, up to 2 ml of semen is added. Once the density gradient is constructed, the cap 135 (plastic sticker) on the aspiration (shaft) channel 130 is removed in step 1225 and in step 1230 the tube 200 is capped and the tube 200 including the receiving cylinder 110 and aspiration channel 130 are subjected to 700×g for 30 minutes in order to pellet the sperm sample. After centrifugation, in step 1235 the cap is removed from the tube 200 and the aspiration device 140 (modified micropipette tip) is attached to any standard 100 μl micropipettor and then inserted through the aspiration channel 130 into the bottom of the tube 200 where the sample pellet is located and the sample pellet is aspirated through the aspiration device 140. Finally, in step 1240 the tube is re-capped and disposed of as biohazardous waste. The amount of solution, speed and time of centrifugation, sperm preparation device, and the like may be altered depending on the amount of sample, use, or the like.

Figure 13:
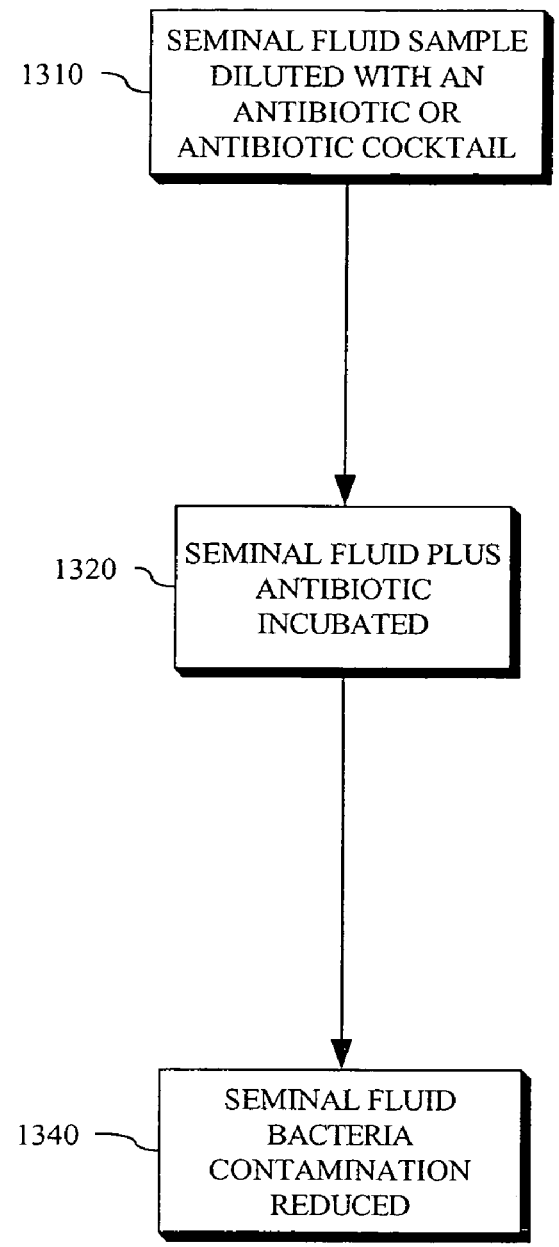
FIG. 13 is a block diagram illustrating an exemplary method of the present invention wherein decontamination of a seminal fluid sample occurs through the use of an antibiotic and enzyme treatment.
Figure 14:
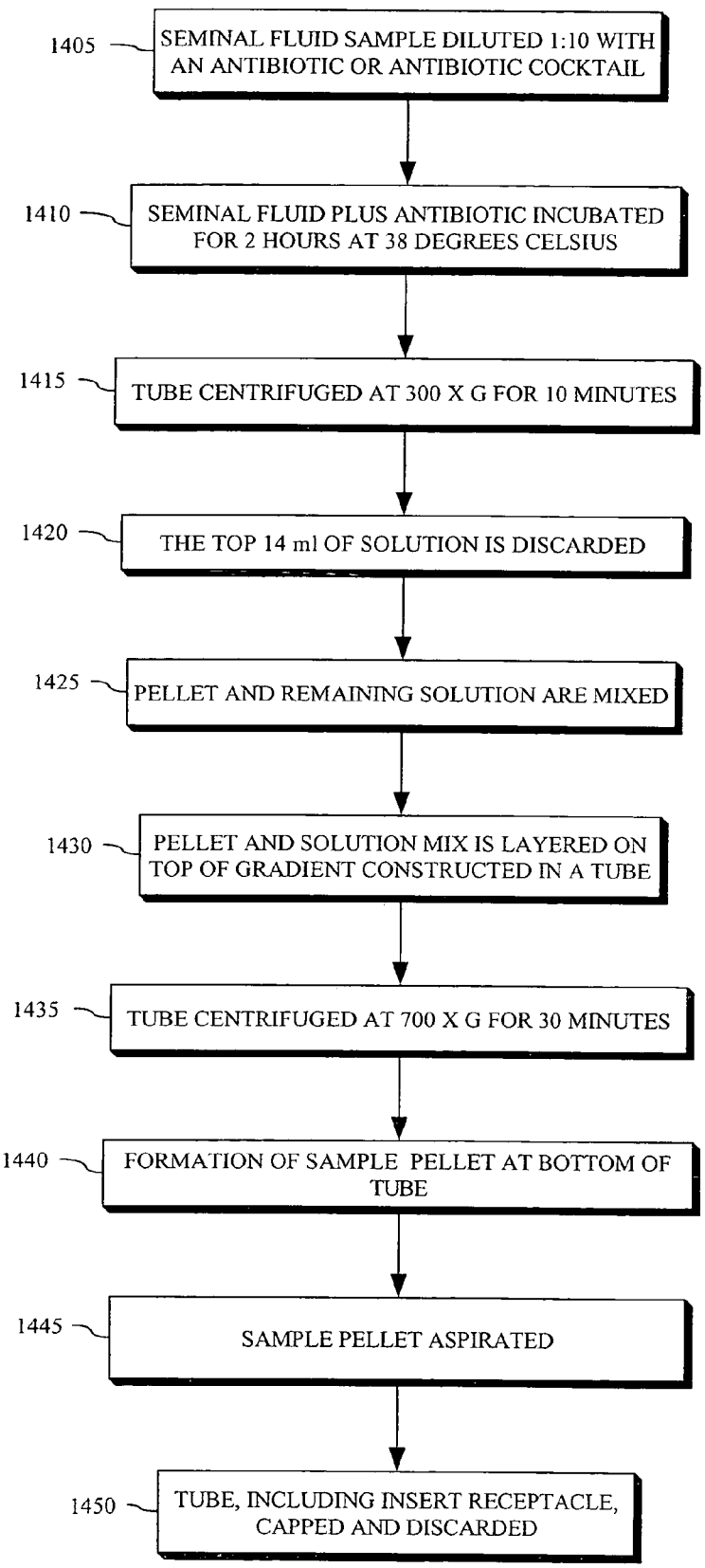
FIG. 14 is a block diagram illustrating an exemplary method of the present invention wherein decontamination of a seminal fluid sample occurs using antibiotic and enzyme treatments and then the decontaminated sample pellet is aspirated.
Figure 16:
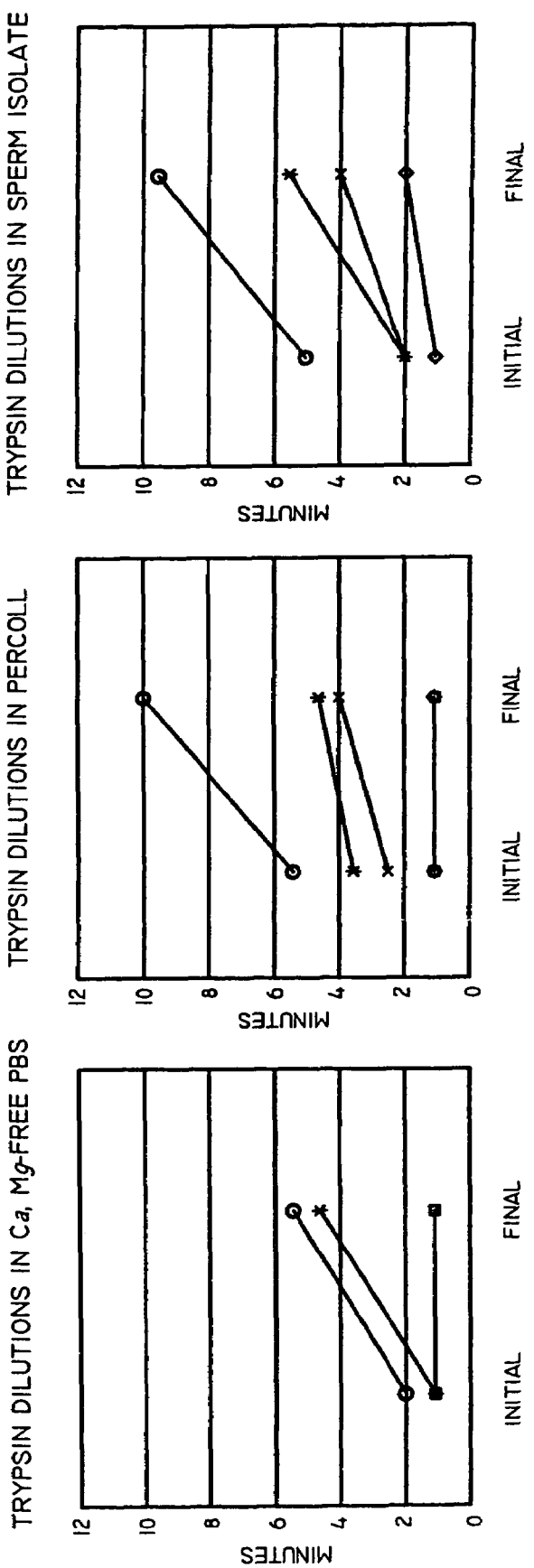
FIGS. 16 and 17 are graphical representations illustrating the effect that diluting trypsin with various reagents has on detachment of confluent buffalo rat liver cell monolayers.
Figure 17:
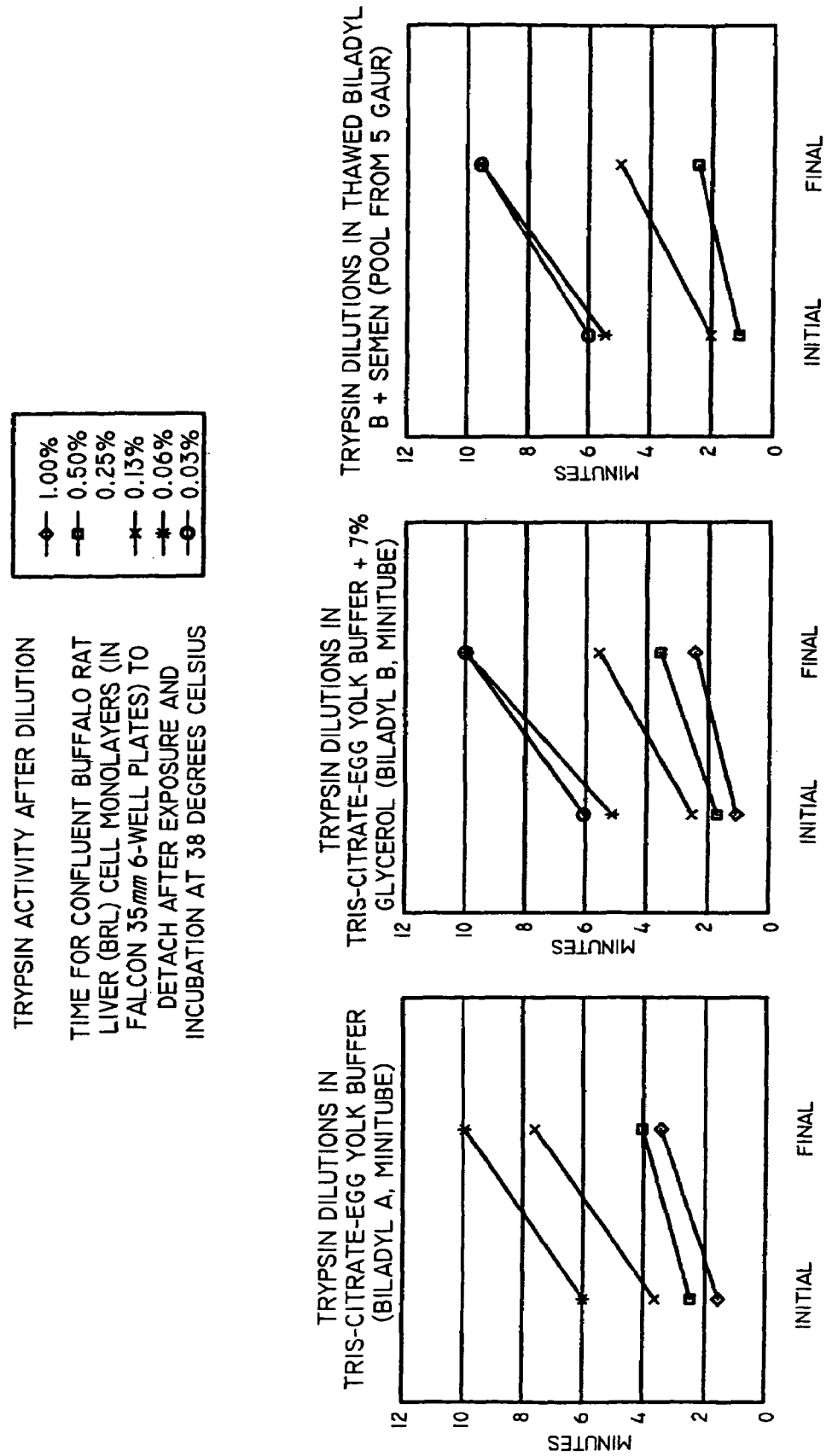

FIG. 13 shows a method of treating a sample for the reduction of contamination by bacteria. In a first step 1310 a seminal fluid sample is diluted with an antibiotic or antibiotic cocktail in a tube, such as tube 200. Antibiotic is defined as anything that will inactivate bacteria as a pathogenic agent. The dilution of seminal fluid to antibiotic may be 1:10 (FIG. 14). This ratio may change depending on the virus, antibiotic used, and ultimate use of the seminal fluid. The cocktail may include one or more of the following: Gentamycin, Specinomycin, Lincomycin, Tylosin, Kanamycin, and any other appropriate antibiotic. By adding antibiotic, bacteria may be reduced or eliminated from seminal fluid. In step 1320, the seminal fluid plus antibiotic is incubated at physiological temperature for approximately 2 hours (FIG. 14). This incubation may be effective in reducing or eliminating bacteria contamination in the seminal fluid. The temperature and time may be altered depending on the bacteria and antibiotic used. In step 1330 the decontaminated seminal fluid sample is prepared, wherein the bacteria presence has been reduced or eliminated from the sample. In most cases, this method will eliminate any bacteria susceptible to the antibiotics applied. This method is effective and does not harm the sperm cell function. This method is beneficial as it may be used on both animal and human seminal fluid.

Referring now to FIG. 14 an additional method of decontaminating a seminal fluid sample is shown. In a first step 1405 a seminal fluid sample is diluted with an antibiotic or antibiotic cocktail in a tube, such as tube 200. The dilution of seminal fluid to antibiotic is 1:10. In a second step 1410 the seminal fluid plus antibiotic is incubated at thirty eight degrees Celsius (38° C.) for 2 hours. Following the incubation period, in step 1415 the tube is centrifuged at a speed of 300×g for ten (10) minutes. After the centrifugation, the top fourteen milliliters (14 ml) of solution is discarded in step 1420, leaving approximately one milliliter (1 ml). Then, in step 1425, the pellet and remaining solution are mixed. In step 1430 the pellet and solution gathered from step 1425 is layered on top of a gradient constructed in another tube, such as the gradient constructed in the tube 200 as shown and described in reference to FIG. 12. The gradient established for use in step 1430 includes a colorant with Layer 2 and the trypsin inactivator is a soy-based trypsin inactivator. It is to be understood that the gradient of FIG. 12 may also include these specific chemical compounds without departing from the scope and spirit of the present invention. After layering the pellet and solution from step 1425 into the tube in step 1430, the tube is centrifuged at 700×g for thirty (30) minutes in step 1435. The centrifugation, in step 1440, results in a second pellet of decontaminated sperm forming at the bottom of the tube. The second pellet is aspirated in step 1445 utilizing an aspiration device, such as aspiration device 130. Then in step 1450 the tube is capped and discarded in a biohazardous waste facility. Speed and time of centrifugation, tube size or shape, and the amount of solution discarded and kept may be changed depending on the antibiotic or specific use for the sperm. Due to the application the sperm is used for, it may be desired that the sperm be more diluted requiring more solution left remaining.

Experiments

A variety of experiments were employed to show the many advantages of the present invention and the unexpected benefits of providing "disinfection" of viruses and/or bacteria from biological samples, examples of which follow.

Sperm Survival after Treatment

In a first experiment, fresh semen was collected from six domestic bulls (Bos taurus) and six gaur (Bos gaur) bulls. Samples were treated in Percoll columns, with (positive control) or without (negative control) trypsin (0.125%) in a 45% column. As a result, there were no detrimental affects of the trypsin treatment as the sperm demonstrated no significant reduction in overall motility, no reduction in viability (as determined using vital staining), nor any significant damage in acrosomal integrity. Acrosomes are the caps on the sperm heads that contain enzymes that aid in penetrating the egg investments during fertilization. Release of these enzymes (termed acrosome reaction) is also associated with hyperactivation of the sperm (where they no longer are progressively motile, but rather, begin a 'figure eight' thrusting movement to add in penetrating the outer glyco protein shell (zona pellucida) surrounding the egg, or oocyte, which should occur only when in close proximity to the oocyte. Therefore, premature acrosome reactions or acrosome damage would limit the effectiveness of the sperm for standard artificial insemination procedures where sperm are deposited into the uterus.

Thus, the semen "disinfection" procedure of the present invention was not detrimental to fresh (non-cryopreserved) bovine semen. It was important then to determine if the procedures worked equally well with cryopreserved semen, and if bovine sperm would survive treatment just prior to cryopreservation, which would be necessary if the procedure would be used to import bovine semen from other countries into the United States. A preliminary study was conducted using pooled semen collected from two domestic bulls (Bos taurus) to determine the spermatozoal viability if treated before or after cryopreservation.

The pooled bovine semen was divided into six treatment groups: (1) raw (no further processing); (2) raw, fresh, washed; (3) raw, fresh, treated; (4) treated then cryopreserved; (5) cryopreserved then treated; and (6) cryopreserved only. The "washed" treatment incorporated medium without antibiotics and Percoll density gradient centrifugation without trypsin, and the "treated" groups used the antibiotic cocktail in the medium and 0.125% trypsin in the 45% Percoll layer. The results of this preliminary study are summarized in Table 2.

TABLE 2

Bovine sperm survival after semen "disinfection" treatment procedure (and control washes) before or after cryopreservation using a standard bovine method.

| | % Motility | | | Kinetic Ratings[1] | | % Viability[2] | | % Acrosome Intact[2] | | |
|---|---|---|---|---|---|---|---|---|---|---|
| | 0 h | 2 h | 20 h | 0 h | 2 h | 0 h | 2 h | 0 h | 2 h | % IVF[3] |
| Raw (fresh) | 95 | 90 | 0 | 3 | 3 | 95 | 85 | 95 | 90 | NA |
| Fresh, wash | 100 | 80 | 40* | 3 | 4 | 84 | 78 | 83 | 78 | 80 (n = 15) |
| Fresh, treat | 100 | 90 | 60* | 4 | 3.5 | 78 | 82 | 79 | 75 | 66 (n = 18) |
| Treat, freeze | 60 | 20 | 0 | 3 | 2.5 | 64 | 44 | 56 | 43 | 62 (n = 8) |
| Freeze, treat | 80 | 60 | 20* | 3 | 3 | 50 | 65 | 66 | 50 | 53 (n = 17) |
| Freeze only | 80 | 50 | 10 | 4 | 3.5 | 72 | 60 | 72 | 65 | 60 (n = 15) |

[1]Rate of forward progression (0 = no movement, to 5 = fast, linear progression).
[2]As determined by vital staining (Eosin B/Fast Green).
[3]In vitro-matured bovine oocytes, 18 hours post-insemination (whole mount, aceto-orcein); data reflects only monospermic (2 pronuclei) fertilization.
*Sperm head agglutination observed.

As a result it appears that bovine sperm survive the semen "disinfection" procedure of the present invention both before and after the application of cryopreservation. It is understood that the semen "disinfection" procedure may have increased effectiveness if applied after cryopreservation of the sperm. However, application of the semen "disinfection" procedure before cryopreservation may allow for the import of bovine semen from other countries into the United States.

Efficacy of Procedure for Eliminating Specific Pathogenic Agents:

A. Treatment of Semen Inoculated with Known Pathogens

Although a great deal of research has been conducted in South Africa on developing successful protocols for cryopreserving sperm collected from hunted game species, none of the cryopreserved samples have ever been transported to the USA owing to USDA APHIS restrictions to the importation of tissues from animals in South Africa (and especially in Kruger National Park, which is regarded as endemic to viral diseases such as Foot-and-Mouth disease and rinderpest, which do not occur in North America). In light of the possible closure of the Poland quarantine station mentioned previously (and the devastating consequence this would have on any future importation of ungulates and suids from Africa and Asia into North America) as well as the bounty of potential genetic material that can be made available from game species hunted annually in South African National Parks (potentially for use in artificial insemination programs in North American zoos), a project was designed to test the efficacy of the semen "disinfection" method of the present invention on ejaculate collected from free-ranging, African (Cape) buffalo (*Syncerus caffer*).

African buffalo were chosen as the animal model for this initial trial of the semen "disinfection" method of the present invention for two primary reasons: (1) Kruger National Park was beginning a massive eradication program in the year 2000 A.D. to cull and hunt buffalo infected with tuberculosis (*Mycobacterium bovis*)—the goal was to capture and test 1,000 buffalo each year for five years (2000 A.D.-2004 A.D.), therefore, semen could be collected from animals known to have tuberculosis; and (2) African buffalo at Kruger National Park are known to be carriers of Foot-and-Mouth Virus, yet the African buffalo do not develop the clinical symptoms typical of the disease in domestic livestock (which can be economically devastating—as has recently been experienced by the Foot-and-Mouth Virus outbreak in Europe). The officials at Kruger National Park approved the proposal as realization of the great potential for the development of a semen "disinfection" method that may serve as a possible means for salvaging at least the genetic material from animals infected with tuberculosis before the animals are culled and hunted, as a long-term conservation strategy.

In light of the global interest in the Foot-and-Mouth Virus, the buffalo may also serve as a valuable model to test the effectiveness of the semen "disinfection" procedure on known, infected animals. A third objective was added to the Kruger National Park project, at the request of the park officials, to evaluate the effectiveness of the semen "disinfection" method of the present invention on *Brucellosis*. A large percentage of the buffalo at Kruger National Park were also suspected, and later found, to be infected with *Brucella abortus*—another serious bacterial disease that causes spontaneous abortions in buffalo as well as domestic livestock.

Although the results of the preliminary experiments (described above) demonstrated that the semen "disinfection" procedures of the present invention did not appear to be detrimental to sperm, it was equally important in the first phase of the buffalo investigation to determine if the procedure was also effective in removing the specific pathogens of interest (i.e., *Mycobacterium bovis*, Foot-and-Mouth Virus, and *Brucella abortus*).

To accomplish the goal of this initial phase, semen samples were collected from six African buffalo on a game ranch in South Africa, believed to be "disease-free" by the game manager. Those six samples were submitted to the Onderstepoort Veterinary Institute and each were divided into five aliquots. One aliquot of each raw semen sample was kept as the negative control, while the other four aliquots were individually inoculated with higher than physiological doses of the pathogens: (1) *Brucella abortus*, (2) *Campylobacter* species, (3) *Mycobacterium bovis*, and (4) Foot-and-Mouth Virus.

The raw semen and inoculated semen aliquots for all six buffalo were then processed in four treatment groups: 1) raw semen (negative control); 2) inoculated semen (positive control); 3) inoculated semen washed only (i.e., 2 hour incubation at 38° C. in medium without antibiotics, then Percoll density gradient centrifugation without trypsin; and 4) inoculated semen treated by 2 hour incubation at 38° C. in medium containing the antibiotic cocktail, then Percoll density gradient centrifugation using 0.125% trypsin in the 45% layer.

The final analyses for the presence of *Brucella abortus*, *Campylobacter* species and Foot-and-Mouth Virus has been completed and the results were similar for all three pathogen groups: 1) the non-inoculated raw semen (negative control) aliquots were all negative for the respective pathogens; 2) the inoculated raw semen (positive control) aliquots were all positive for the respective pathogens; 3) the washed only inoculated semen aliquots were mostly all positive (one of the six bull ejaculates inoculated with *Campylobacter*, and two of the ejaculates inoculated with Foot-and-Mouth Virus, were negative after simple washing); and 4) the inoculated raw semen aliquots treated with the antibiotic cocktail and trypsin were all negative.

The results of the *Brucella abortus*-inoculated semen samples indicate that the semen "disinfection" procedure of the present invention was effective for eliminating two bacterial pathogens, *Brucella abortus* and *Campylobacter* species, and one viral pathogen, Foot-and-Mouth Virus, from buffalo semen samples that were experimentally inoculated with doses much higher than what would occur physiologically.

Efficacy of Procedure for Eliminating Specific Pathogenic Agents:

B. Treatment of Semen Collected from Infected Animals

The next phase of this study was to test the procedure on ejaculates collected from free-ranging buffalo at Kruger National Park known to be infected with *Brucella abortus*, Foot-and-Mouth Virus, and also *Mycobacterium bovis*. This investigation was actually initiated with semen samples collected from approximately 60 free-ranging buffalo. Those samples were aliquoted and divided into three treatment groups: (1) raw semen; (2) washed semen (no antibiotics in the medium using for the 2 hour incubation and no enzymes added to the Percoll density gradient centrifugation); and (3) treated semen (2 hour incubation at 38° C. in the antibiotic cocktail followed by Percoll density centrifugation with trypsin in the 45% layer). All treated aliquots for each buffalo were then cryopreserved and stored in liquid nitrogen until the results were known from the phase one investigation (treatment of the buffalo semen inoculated with the different pathogenic agents).

After conducting the first phase of experiments in South Africa and the results indicated that the semen "disinfection" procedure was effective in eliminating bacteria such as *Brucella abortus* and *Campylobacter* species from buffalo semen inoculated with those pathogenic agents, the effect of the addition of other antibiotics on the effectiveness of the original cocktail to treat different microorganisms was evaluated. There were, however, two main concerns associated with this modification of a CSS-approved antibiotic cocktail: (1) adding new antibiotics may attract the attention of veterinary regulatory agencies that are extremely sensitive to the overuse or abuse of novel antibiotics that may end up in food animals; and (2) certain antibiotics at specific concentrations can be detrimental to sperm.

The first concern is valid since it can be argued that the semen "disinfection" procedure may be used in the propagation of livestock by artificial insemination, so (theoretically) residual antibiotics may be injected into inseminated females via treated sperm. If this were the case, then resistant strains of bacteria may result in the inseminated females, which ultimately would negate the potential benefits of the novel antibiotic(s). Nevertheless, by design, the sperm processing procedure involving silane-coated, silica particle (Isolate, Irvine Scientific) density gradient centrifugation separates the viable sperm from the holding medium, whether that be seminal plasma or medium containing antibiotics, into the 90% column of Isolate. Thus, such concern is minimized.

The second concern is based on published reports of antibiotic efficacy and toxicity to sperm and other cell types. Some of these reports provide a variety of antibiotics and ranges of concentrations that are tolerated in standard cell cultures and do not affect the in vitro development of murine embryos or bovine embryonic cell lines at a standard incubation temperature of 37° C. One antibiotic which was tested, kanamycin, showed very little toxicity to cultured cells and embryos even at relatively high concentrations (up to 1000 µg/ml). Since kanamycin is an accepted antibiotic supplement in commercial medium products used for embryo collection and transfer, the decision was made to add kanamycin to the semen "disinfection" procedure at the maximal concentration of 1000 µg/ml. In addition, 200 µg/ml of tylosin was included in the modified protocol for the semen "disinfection" procedure. Tylosin is already included in the CSS-recommended antibiotic cocktail formulation at a concentration of 100 µg/ml. Further, previous studies had demonstrated that a concentration of 200 µg/ml of tylosin was capable of eliminating a *Mycoplasma* species (a non-bacterial, non-viral pathogenic agent) from bovine embryos without effecting embryo viability. For this reason, the tylosin concentration in the semen "disinfection" procedure was increased to 200 µg/ml in the modified protocol.

To test the effect of the modified antibiotic cocktail on the viability of bovine sperm, the following study was performed. Semen was collected from three domestic bulls and after initial characterization, the semen was diluted 1:10 in the modified antibiotic cocktail, and then incubated for 2 hours at 38° C. After incubation, the diluted semen was gently mixed and an aliquot was removed for examination. The remaining volume was centrifuged at 300×g in order to concentrate the treated sperm. Following centrifugation, an aliquot was removed for examination as well as to inseminate a group of in vitro matured bovine oocytes. Results indicate no significant increases in acrosome reactions at two hours post-treatment. The post-treatment estimations of progressive sperm motilities and fertilization of bovine oocytes by treated sperm are summarized in the following table.

TABLE 3

Results of trial using modified antibiotic cocktail on fresh semen collected from each of three domestic bulls. Data is presented as overall percentage of sperm motility at 0, 2 and 22 hours or percentage sperm penetration (IVF) of bovine oocytes 18 hours post-insemination.

| | Raw | | Washed (pre-spin) | | | Washed | | Treated (pre-spin) | | | Treated | |
|---|---|---|---|---|---|---|---|---|---|---|---|---|
| | 0 h | 2 h | 0 h | 2 h | 22 h | 0 h | 2 h | 0 h | 2 h | 22 h | 0 h | 2 h |
| Bull1 | 95 | 90 | 90 | 90 | 40 | 90 | 90 | 90 | 80 | 20 | 90 | 80 |
| Bull2 | 95 | 95 | 90 | 90 | 60 | 90 | 90 | 90 | 80 | 15 | 90 | 80 |
| Bull3 | 90 | 85 | 90 | 90 | 0 | 80 | 80 | 90 | 90 | 10 | 80 | 80 |

Addition of Trypsin Inactivator to Prevent Enzyme Activity

One problem with the density gradient centrifugation technique for processing sperm is the potential of mixing gradient layers during gradient formation or aspiration of the pellet following centrifugation. If the 45% isolate layer containing active trypsin is inadvertently mixed with the 90% layer containing the sperm pellet, sperm viability may be affected because of increased exposure to trypsin. The present investigator decided to avoid this risk by adding a trypsin inhibitor to the 90% layer. Studies were performed utilizing a soy-based product in order to eliminate the concern of possible pathogen contamination from an animal based product. In the initial trials with this product, using cryopreserved gaur (*Bos gaurus*) sperm, the recommended guidelines provided by Sigma Chemical Company (St. Louis, Mo.) were followed. In brief, 1.4 mg of the inhibitor was used for every 1 mg of trypsin. However, initial results indicated that the thawed gaur sperm were not surviving beyond one hour post-exposure at the suggested concentration. Therefore, a dose-response study was performed (on the detachment of confluent somatic cell monolayers) to determine the minimal concentration of the soy-based inhibitor necessary to inactivate two concentrations of trypsin: 0.125% and 0.25%. As summarized in FIG. 15, the results indicated that the minimal concentration to achieve complete inactivation of trypsin was generally 10 µg/ml (which is almost 200 times less concentrated than that suggested by Sigma Chemical Co.).

A trial was then conducted using the inactivator at the lower concentration on fresh semen collected from each of three domestic bulls. When added to the 90% Isolate at 10 µg/ml, the soy-based trypsin inactivator had no detrimental effect on bovine sperm motility, viability and acrosomal integrity, as summarized in Table 4A and 4B, below.

As indicated by the results, there were no significant differences between the three bull sperm populations that were treated with Isolate gradient centrifugation without trypsin and the soy-based trypsin inhibitor, or with 0.25% trypsin in the 45% layer and 10 µg/ml soy-based trypsin inactivator in the 90% layer. Because of the benefits of using this enzyme inhibitor, the semen "disinfection" procedure was modified to include this product in an embodiment of the present invention.

Preliminary Trials on Boar Semen

In light of the preference for the BTS medium for boar semen, a preliminary study was first performed on the pooled semen to determine if BTS was more optimal than the TL Hepes Solution (used in the semen "disinfection" procedure) for use with swine. A 1:5 dilution (semen:medium) was made using: 1) TL Hepes Solution; 2) TL Hepes Solution containing the modified antibiotic cocktail; 3) BTS medium (which does not contain bovine serum albumin nor phenol red); and 4) BTS medium containing the modified antibiotic cocktail. The four treatments were incubated at 39° C. (physiological

TABLE 4A

Effect of incubation of fresh bovine sperm in 90% Isolate without the addition of soy-based trypsin inactivator, and without trypsin in the 45% layer.

| | Raw | | Isolate without trypsin or inactivator 0 h | | | | Isolate without trypsin or inactivator 2 h | | | | Isolate without trypsin or inactivator 22 h | | | |
|---|---|---|---|---|---|---|---|---|---|---|---|---|---|---|
| | 0 h | 2 h | Mot | KR | Live | AI | Mot | KR | Live | AI | Mot | KR | Live | AI |
| Bull1 | 95 | 90 | 80 | 3 | 78 | 79 | 90 | 4 | 91 | 92 | 20 | 3 | — | — |
| Bull2 | 95 | 95 | 80 | 3 | 77 | 82 | 90 | 4 | 75 | 87 | 10 | 2 | — | — |
| Bull3 | 90 | 85 | 80 | 3 | 77 | 88 | 60 | 3 | 82 | 82 | 10 | 3 | — | — |

Key:
Mot = overall % motility; KR = kinetic rating (0 = no movement to 5 = fast, linear movement; Live = % viable by vital staining; AI = % acrosome intact.

TABLE 4B

Effect of incubation of fresh bovine sperm in 90% Isolate, with the addition of 10 g/ml soy-based trypsin inactivator, and with 0.25% trypsin in the 45% layer.

| | Raw | | Isolate with trypsin + inactivator 0 h | | | | Isolate with trypsin + inactivator 2 h | | | | Isolate with trypsin + inactivator 22 h | | | |
|---|---|---|---|---|---|---|---|---|---|---|---|---|---|---|
| | 0 h | 2 h | Mot | KR | Live | AI | Mot | KR | Live | AI | Mot | KR | Live | AI |
| Bull1 | 95 | 90 | 80 | 3 | 84 | 85 | 60 | 3 | 78 | 82 | 10 | 1 | — | — |
| Bull2 | 95 | 95 | 80 | 3 | 76 | 78 | 60 | 3 | 84 | 85 | 10 | 2.5 | — | — |
| Bull3 | 90 | 85 | 80 | 4 | 72 | 72 | 80 | 3 | 73 | 84 | 0 | 0 | — | — |

Key:
Mot = overall % motility; KR = kinetic rating (0 = no movement to 5 = fast, linear movement; Live = % viable by vital staining; AI = % acrosome intact.

temperature for pigs) and then, the diluted sperm were concentrated by centrifugation at 300×g for 10 min and evaluated. The results are summarized in Table 5, below.

TABLE 5

Initial trial incubating 10 ml pooled boar semen (0.648 × 10$^9$/ml) in two different media, with and without the supplementation of antibiotic cocktail, then centrifuged for 10 min at 300 × g and examining sperm characteristics, aspirating and discarding supernatant and reconstituting the sperm-rich pellet in 5 ml remaining medium (Note: final sperm concentrations in the washed 5 ml are essentially similar to starting concentration in 10 ml).

| | Sperm | | Acrosomal Integrity* | | | |
|---|---|---|---|---|---|---|
| | Conc × 10$^9$/ml* | % Prog Motile | % Normal | % Damaged | % Missing | % Loose |
| TL Hepes | — | 85 | — | — | — | — |
| TL Hepes + Ab | 1.233 | 85 | 97 | 0 | 2 | 1 |
| BTS | — | 90 | — | — | — | — |
| BTS + Ab | 1.186 | 90 | 96 | 1 | 2 | 1 |

*Only performed on those treated in the presence of the antibiotic (Ab) cocktail.

Essentially, there was no immediate difference with the TL Hepes Solution versus the BTS medium for incubating boar sperm with or without the supplementation of the antibiotic cocktail. The 5 ml washed sperm concentrate from both medium groups was then placed on a modified Isolate density gradient column (the design was made after a preliminary trial using the standard 2 ml columns of 45% and 90% in a 15 ml conical tube was found not to provide enough volume necessary to separate the large concentration of viable boar sperm in the pooled ejaculate, and that would be needed for a standard insemination dose of approximately 5×10$^9$ sperm—diluted in a total volume of 100 ml semen with or without extender).

The results of the boar sperm characteristics of aliquots incubated initially in either the TL Hepes Solution or the BTS medium supplemented with the antibiotic cocktail, then concentrated to 5 ml by centrifugation at 300×g for 10 min and processed through the isolate density gradient centrifugation (700×g for 30 min) are summarized in Table 6 (Note: the sperm pellet was reconstituted in the approximately 10 ml of 90% Isolate containing 20 μg/ml soy-based trypsin inactivator and incubated at room temperature):

TABLE 6

Boar sperm characteristics after the antibiotic treatment - cocktail supplemented to either TL Hepes Solution or BTS medium; Note: TL Hepes contains 3 mg/ml BSA, BTS contains no protein) then Isolate gradient centrifugation using 0.25% trypsin in the 45% layer. The sperm pellet was reconstituted in the remaining 10 ml of Isolate and incubated at room temperature (on the bench top) for the periods indicated.

| | | Sperm | | Acrosomal Integrity* | | | |
|---|---|---|---|---|---|---|---|
| | Hours incubation | Conc × 10$^9$/ml* | % Motility | % Normal | % Damaged | % Missing | % Loose |
| TL Hepes | 0 (3 pm) | 1.2 | 55 Progressive | 94 | 1 | 3 | 2 |
| | 5 (8 pm) | — | 60 Progressive | 98 | 0 | 2 | 0 |
| | 17 (8 am) | — | 20 Non-Progress | — | — | — | — |
| BTS | 0 (3 pm) | 0.97 | 80 Progressive | 97 | 1 | 0 | 2 |
| | 5 (8 pm) | — | 60 Progressive | 94 | 0 | 6 | 0 |
| | 18 (8 am) | — | 10 (Half Progess) | — | — | — | — |

*Concentration of pooled raw semen (before dilution) = 0.648 × 10$^9$/ml; Concentration after 2 h incubation with Ab then concentration (300 × g, 10 min) to 5 ml: TL Hepes: 1.233 × 10$^9$/ml and BTS: 1.186 × 10$^9$/ml.

Domestic Cattle

A second trial was conducted on domestic bull semen. A total of 10 samples were provided and the semen disinfection procedure was performed blindly without knowing which of the samples contained pathogens. In the group of 10 semen samples, two samples came from bulls persistently infected with bovine viral diarrhea (BVD) virus, four samples from bulls acutely infected with BVD virus, and two samples from healthy bulls served as the negative controls.

After treatment, the samples were assayed by using two procedures: (1) virus isolation that detects active virus (cytotoxic effects) and (2) polymerase chain reaction which detects the presence of any of both active and inactive viral particles. The results were as follows:

| Sample # | Virus used | virus isolation | PCR |
|---|---|---|---|
| 1 | BVDV-persistent | Looks + ?? | +/+ |
| 2 | BVDV-persistent | looks Neg ?? | neg |
| 3 | BVDV-acute | looks Neg ?? | neg |
| 4 | BVDV-acute | looks + ?? | neg |
| 5 | BVDV-acute | looks Neg?? | neg/+ |
| 6 | BVDV-acute | looks Neg ?? | +/neg |
| 7 | Neg control | neg | neg |
| 8 | Neg control | neg | neg |

As a result of the application of the method of the present invention, it is seen that many of the bulls acutely infected with BVD, were cleared of the virus.

A study was conducted to test the semen "disinfection" procedure of the present invention on domestic bull semen samples inoculated with *Brucella abortus* and *Campylobacter* spp. bacteria. A total of 21 cryopreserved semen samples from several economically important, indigenous breeds of cattle were spiked with the bacteria then processed using the semen disinfection procedure. Each sample was divided into four aliquots: (1) non-inoculated (negative) control; (2) inoculated (positive) control; (3) inoculated—washed (in medium only and centrifuged in Percoll density gradients without added trypsin; and (4) inoculated—treated (in medium containing the antibiotic cocktail and centrifuged in Percoll density gradients containing trypsin). The treated sperm resulting from all four treatments for the semen samples from each of the 21 bulls were then streaked onto agar plates and incubated for 3-5 days to allow bacterial growth. The 21 "treated" samples (treatment 4 above) were also submitted for antibiotic residue analysis (gentamycin, spectinomycin, lincomycin, tylosin and kanamycin). This last step was important to prove that there would be no residual antibiotics present in the treated sperm sample that could be transferred to a recipient cow during an artificial insemination procedure. The results from the bacterial cultures for the four treatments are shown as follows:

Bacterial Culture of the Semen of Indigenous African Cattle Breeds

Bacterial cultures provided: (1) *Brucella abortus* Strain 19 [vaccine strain]—suspension at $10^8$/ml and (2) *Campylobacter fetus*—recent laboratory isolate [4914] from a bull in an infected herd in the Kuruman district—suspension at $10^7$/ml. 0.1 ml of each suspension was added to the semen samples (i.e. both *Brucella* and *Campylobacter* were added to one tube of semen). Both isolates were found to be sensitive to several of the antibiotics used in the novel disinfection procedure. *B. abortus* was sensitive to gentamicin, kanamy- cin and spectinomycin, intermediate to tylosin and resistant to lincomycin. *C. fetus* was sensitive to gentamicin, kanamycin and lincomycin, and intermediate to tylosin and spectinomycin. At the end of the procedure, all 84 samples of semen taken from the 21 bulls were cultured on duplicate blood tryptose agar plates, prepared with bovine blood by Onderstepoort Biological Products. One plate was incubated in 5% $CO_2$ in air, while the other was cultured in an anaerobic pot containing gas generating sachets [Oxoid, BR 56/60].

The results of culture were as follows:

| Sample no. | N | P | W | T |
|---|---|---|---|---|
| 1 | N | C & B | B | N |
| 2 | N | B | N | N |
| 3 | N | B | N | N |
| 4 | N | N | N | N |
| 5 | N | B | B | N |
| 6 | N | B | N | N |
| 7 | N | C & B | N | N |
| 8 | N | C & B | N | N |
| 9 | N | B | N | N |
| 10 | N | C & B | N | N |
| 11 | N | C & B | N | N |
| 12 | N | N | B* | N |
| 13 | N | B | B | N |
| 14 | N | B | B | N |
| 15 | N | C & B | N | N |
| 16 | N | C & B | N | N |
| 17 | N | C & B | N | N |
| 18 | N | C & B | N | N |
| 19 | N | C & B | N | N |
| 20 | N | N | N | N |
| 21 | N | C & B | N | N |

Headers N, P, W and T - as in protocol
In table - N = negative; C = growth of *C. fetus*; B = growth of *Brucella*
*= only one colony isolated The semen disinfection procedure was successful in eliminating the two species of bacteria from bull semen inoculated with the organisms. An interesting outcome of this experiment was that simply "washing" the sperm in medium without antibiotics and centrifuging through the Percoll layers without trypsin was completely effective for eliminating *Campylobacter* spp., but not totally effective for removing *Brucella abortus* (5 of the 21 washed samples contained the bacteria). Another interesting and unexpected outcome was in the inoculated (positive) controls, 3 tested negative for both types of bacteria and 7 of the 21 tested negative for *Campylobacter* spp., but positive for *Brucella abortus*. This can be explained by the fact that we were using cryopreserved semen which is typically frozen using diluents that contain antibiotics. That being the case, all of the 21 samples should have shown negative results as the antibiotics in the cryodiluents should have killed the bacteria that was placed into the diluted semen sample during the approximately four hour room temperature incubation period prior to agar streaking. A possible explanation for the observed results is that the antibiotics in the cryopreserved semen samples had degraded over time and lost activity. Further, it is also possible that the amount of bacteria that was placed into the sample overwhelmed the amount of antibiotics present.

Poultry

A trial was conducted on rooster and turkey semen. Research has found that the bacteria *Salmonella* spp. and *Campylobacter* spp., which are problematic in poultry production, can be transmitted sexually to the egg yolk from the semen of infected males. At the time of the trial, testing was being performed on several new types of commercial media containing novel antibiotic preparations. Such studies found that none of the then currently available medias were completely effective for removing *Salmonella* spp. In subsequent trials, employment of the antibiotic cocktail present in the semen "disinfection" technique of the present invention resulted in the complete elimination of both *Campylobacter* spp. and *Salmonella* spp.

Swine

Semen was collected from a total of 18 boars from a stud that recently had an outbreak of the porcine reproductive and respiratory syndrome (PRRS) virus. The semen was extended in a boar semen diluent, and subjected to the semen "disinfection" procedure of the present invention following overnight transport. Samples of the 18 untreated and treated samples were then sent for PCR analysis. Four of the 18 untreated samples were reported as "suspect" for the PRRS virus, whereas all of the 18 treated samples were negative.

Owing to the current level of concern by boar producers regarding the PRRS virus outbreak, specific efforts are being made to reduce the costs of the procedure by treating whole ejaculates before they are divided into artificial insemination doses and transported to farms. The present invention may provide an increased ease of performing such "whole ejaculate" analysis with the novel insert receptacle through which the gradient decontamination procedure is utilized.

It is understood that the specific order or hierarchy of steps in the methods disclosed are examples of exemplary approaches. Based upon design preferences, it is understood that the specific order or hierarchy of steps in the method can be rearranged while remaining within the scope and spirit of the present invention. The accompanying method claims present elements of the various steps in a sample order, and are not necessarily meant to be limited to the specific order or hierarchy presented.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A method for removing a biological sample pellet from surrounding media of a biological sample while reducing the risk of recontamination of the pellet with surrounding media, comprising:

decanting the biological sample through a receiving cylinder into a tube, the receiving cylinder facilitating the slow release of the biological sample into the tube;

passing the biological sample through a multi-layered gradient in the tube, the multi-layered gradient for removing at least one pathogen from the biological sample; and aspirating through an aspiration device a biological sample pellet formed from passing the biological sample through the multi-layered gradient, wherein the aspiration device is inserted into the sample pellet through an aspiration channel integrally related to the receiving cylinder to provide a non-contaminated environment from which to remove the biological sample pellet.

2. The method of claim 1, wherein the step of passing the biological sample through a multi-layered gradient includes centrifuging the receiving cylinder, tube, and biological sample.

* * * * *